US007368098B2

(12) United States Patent
Mueller et al.

(10) Patent No.: US 7,368,098 B2
(45) Date of Patent: May 6, 2008

(54) USE OF BIOMOLECULAR TARGETS IN THE TREATMENT AND VISUALIZATION OF TUMORS

(75) Inventors: Sabine Mueller, San Francisco, CA (US); Mirella Gonzalez-Zulueta, Pacifica, CA (US); Erik Foehr, Novato, CA (US); Daniel J. Chin, Foster City, CA (US)

(73) Assignee: Medarex, Inc., Princeton, NJ (US)

( * ) Notice: Subject to any disclaimer, the term of this patent is extended or adjusted under 35 U.S.C. 154(b) by 472 days.

(21) Appl. No.: 10/328,544

(22) Filed: Dec. 23, 2002

(65) Prior Publication Data

US 2003/0175209 A1 Sep. 18, 2003

Related U.S. Application Data

(60) Provisional application No. 60/343,422, filed on Dec. 27, 2001.

(51) Int. Cl.
*G01N 33/574* (2006.01)

(52) U.S. Cl. .................. 424/1.49; 435/4; 435/7.23

(58) Field of Classification Search ............... 424/1.49; 435/4, 7.1
See application file for complete search history.

(56) References Cited

FOREIGN PATENT DOCUMENTS

| EP | 1033404 A1 * | 9/2000 |
|----|--------------|--------|
| WO | WO 00/20590 | 4/2000 |
| WO | WO 0020590 A2 * | 4/2000 |

OTHER PUBLICATIONS

Mariani et al.; Glioma Cell Motility is Associated With Reduced Transcription of Proapoptotic and Proliferation Genes: A CDNA Microarray Analysis, J of Neuro-Oncology, (2001), 53: 161-176.

Markert et al. Differential Gene Expression Profiling in Human Brain Tumors, Physiol Genomics, (2001), 5: 21-33.

Kroes et al., The Identification of Novel Therapeutic Targets for the Treatment of Malignant Brain Tumors, Cancer Letters, (2000), 191-198.

Reis et al., Short Communication Genetic Profile of Gliosarcomas, American J of Pathology, (2000), 156: (2) 425-432.

Fredriksson et al., Novel Human G Protein-Coupled Receptors With Long N-Terminals Containing GPS Domains and SER/THR-Rich Regions, FEBS Letters, (2002), 531: 407-414.

Liu et al., GPR56, A Novel Secretin-Like Human G-Protein-Coupled Receptor Gene, Genomics, (1999), 55: 296-305.

Yano et al., Differential Expression of β-Catenin in Human Gliobastoma Multiforme and Normal Brain Tissue, Neurological Research, (2000), 22: 650-656.

Zendman et al., TM7XN1, A Novel Human EGF-TM7-Like CDNA, Detected With MRNA Differential Display Using Human Melonoma Cell Lines With Different Metastatic Potential, FEBS Letters, (1999), 292-298.

\* cited by examiner

*Primary Examiner*—Brandon Fetterolf
(74) *Attorney, Agent, or Firm*—Lahive & Cockfield, LLP; Jane E. Remillard, Esq.

(57) ABSTRACT

The present invention relates to the use of a protein that is differentially expressed in primary brain tumor tissues, as compared to normal brain tissues, as a biomolecular target for tumor treatment therapies. The protein is also expressed in tissues from adenocarcinoma, non-melanoma, and renal carcinoma cells. Immunotherapeutic and immunoimaging agents that specifically bind to an identified brain tumor target protein are provided. The present invention also provides compounds and pharmaceutically acceptable compositions for administration in the methods of the invention.

24 Claims, 4 Drawing Sheets

U87  G122  G140  D566  Lung  Liver  Brain  GBM

TM7XN1

β-Actin

Normal Brain (Score 0.5)     Glioblastoma (Score 3)

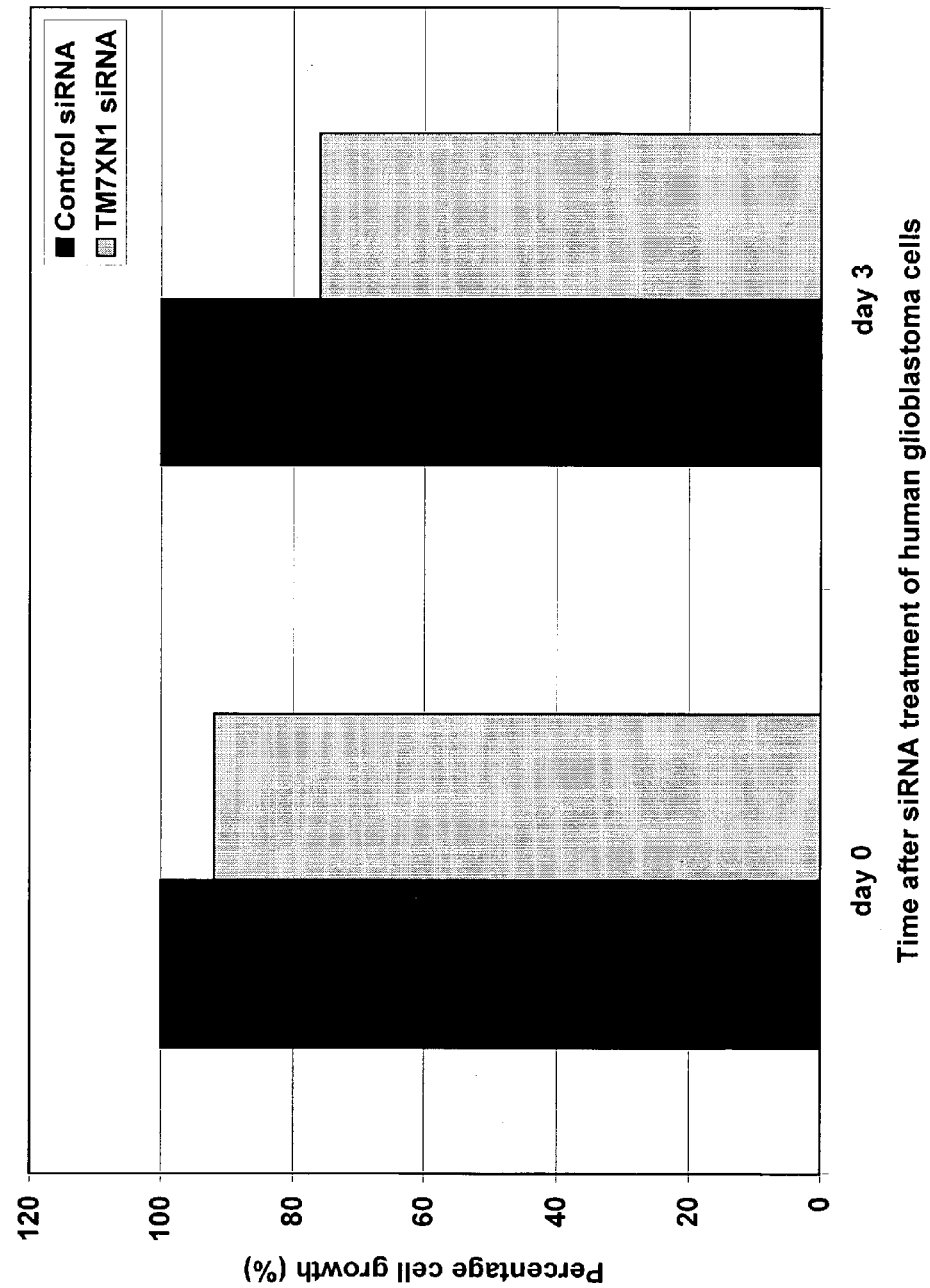

```
                            SEQUENCE LISTING

<160> NUMBER OF SEQ ID NOS: 2

<210> SEQ ID NO 1
<211> LENGTH: 3711
<212> TYPE: DNA
<213> ORGANISM: Homo sapiens
<220> FEATURE:
<221> NAME/KEY: CDS
<222> LOCATION: (168)..(2249)
<223> OTHER INFORMATION:

<400> SEQUENCE: 1
ggcacgaggt ggagggtctc gctctgtcac acaggctgga gtgcagtggt gtgatcttgg      60
ctcatcgtaa cctccacctc ccgggttcaa gtgattctca tgcctcagcc tcccgagtag     120
ctgggattac aggtggtgac ttccaagagt gactccgtcg gaggaaa atg act ccc       176
                                                    Met Thr Pro
                                                    1 cag tcg ctg ctg cag acg aca ctg ttc ctg ctg agt ctg ctc ttc ctg       224
Gln Ser Leu Leu Gln Thr Thr Leu Phe Leu Leu Ser Leu Leu Phe Leu
    5                  10                  15 gtc caa ggt gcc cac ggc agg ggc cac agg gaa gac ttt cgc ttc tgc       272
Val Gln Gly Ala His Gly Arg Gly His Arg Glu Asp Phe Arg Phe Cys
20                  25                  30                  35 agc cag cgg aac cag aca cac agg agc agc ctc cac tac aaa ccc aca       320
Ser Gln Arg Asn Gln Thr His Arg Ser Ser Leu His Tyr Lys Pro Thr
                40                  45                  50 cca gac ctg cgc atc tcc atc gag aac tcc gaa gag gcc ctc aca gtc       368
Pro Asp Leu Arg Ile Ser Ile Glu Asn Ser Glu Glu Ala Leu Thr Val
            55                  60                  65 cat gcc cct ttc cct gca gcc cac cct gct tcc cga tcc ttc cct gac       416
His Ala Pro Phe Pro Ala Ala His Pro Ala Ser Arg Ser Phe Pro Asp
        70                  75                  80 ccc agg ggc ctc tac cac ttc tgc ctc tac tgg aac cga cat gct ggg       464
Pro Arg Gly Leu Tyr His Phe Cys Leu Tyr Trp Asn Arg His Ala Gly
    85                  90                  95
```

```
aga tta cat ctt ctc tat ggc aag cgt gac ttc ttg ctg agt gac aaa       512
Arg Leu His Leu Leu Tyr Gly Lys Arg Asp Phe Leu Leu Ser Asp Lys
100             105                 110                 115 gcc tct agc ctc ctc tgc ttc cag cac cag gag gag agc ctg gct cag       560
Ala Ser Ser Leu Leu Cys Phe Gln His Gln Glu Glu Ser Leu Ala Gln
                120                 125                 130 ggc ccc ccg ctg tta gcc act tct gtc acc tcc tgg tgg agc cct cag       608
Gly Pro Pro Leu Leu Ala Thr Ser Val Thr Ser Trp Trp Ser Pro Gln
            135                 140                 145 aac atc agc ctg ccc agt gcc gcc agc ttc acc ttc tcc ttc cac agt       656
Asn Ile Ser Leu Pro Ser Ala Ala Ser Phe Thr Phe Ser Phe His Ser
            150                 155                 160 cct ccc cac acg gcc gct cac aat gcc tcg gtg gac atg tgc gag ctc       704
Pro Pro His Thr Ala Ala His Asn Ala Ser Val Asp Met Cys Glu Leu
165                 170                 175 aaa agg gac ctc cag ctg ctc agc cag ttc ctg aag cat ccc cag aag       752
Lys Arg Asp Leu Gln Leu Leu Ser Gln Phe Leu Lys His Pro Gln Lys
180                 185                 190                 195 gcc tca agg agg ccc tcg gct gcc ccc gcc agc cag cag ttg cag agc       800
Ala Ser Arg Arg Pro Ser Ala Ala Pro Ala Ser Gln Gln Leu Gln Ser
                200                 205                 210 ctg gag tcg aaa ctg acc tct gtg aga ttc atg ggg gac atg gtg tcc       848
Leu Glu Ser Lys Leu Thr Ser Val Arg Phe Met Gly Asp Met Val Ser
            215                 220                 225 ttc gag gag gac cgg atc aac gcc acg gtg tgg aag ctc cag ccc aca       896
Phe Glu Glu Asp Arg Ile Asn Ala Thr Val Trp Lys Leu Gln Pro Thr
            230                 235                 240 gcc ggc ctc cag gac ctg cac atc cac tcc cgg cag gag gag gag cag       944
Ala Gly Leu Gln Asp Leu His Ile His Ser Arg Gln Glu Glu Glu Gln
245                 250                 255 agc gag atc atg gag tac tcg gtg ctg ctg cct cga aca ctc ttc cag       992
Ser Glu Ile Met Glu Tyr Ser Val Leu Leu Pro Arg Thr Leu Phe Gln
260                 265                 270                 275 agg acg aaa ggc cgg agc ggg gag gct gag aag aga ctc ctc ctg gtg      1040
Arg Thr Lys Gly Arg Ser Gly Glu Ala Glu Lys Arg Leu Leu Leu Val
                280                 285                 290 gac ttc agc agc caa gcc ctg ttc cag gac aag aat tcc agc cac gtc      1088
Asp Phe Ser Ser Gln Ala Leu Phe Gln Asp Lys Asn Ser Ser His Val
            295                 300                 305 ctg ggt gag aag gtc ttg ggg att gtg gta cag aac acc aaa gta gcc      1136
Leu Gly Glu Lys Val Leu Gly Ile Val Val Gln Asn Thr Lys Val Ala
            310                 315                 320 aac ctc acg gag ccc gtg gtg ctc acc ttc cag cac cag cta cag ccg      1184
Asn Leu Thr Glu Pro Val Val Leu Thr Phe Gln His Gln Leu Gln Pro
325                 330                 335 aag aat gtg act ctg caa tgt gtg ttc tgg gtt gaa gac ccc aca ttg      1232
Lys Asn Val Thr Leu Gln Cys Val Phe Trp Val Glu Asp Pro Thr Leu
340                 345                 350                 355 agc agc ccg ggg cat tgg agc agt gct ggg tgt gag acc gtc agg aga      1280
Ser Ser Pro Gly His Trp Ser Ser Ala Gly Cys Glu Thr Val Arg Arg
                360                 365                 370 gaa acc caa aca tcc tgc ttc tgc aac cac ttg acc tac ttt gca gtg      1328
Glu Thr Gln Thr Ser Cys Phe Cys Asn His Leu Thr Tyr Phe Ala Val
            375                 380                 385 ctg atg gtc tcc tcg gtg gag gtg gac gcc gtg cac aag cac tac ctg      1376
Leu Met Val Ser Ser Val Glu Val Asp Ala Val His Lys His Tyr Leu
            390                 395                 400 agc ctc ctc tcc tac gtg ggc tgt gtc gtc tct gcc ctg gcc tgc ctt      1424
Ser Leu Leu Ser Tyr Val Gly Cys Val Val Ser Ala Leu Ala Cys Leu
405                 410                 415
```

```
gtc acc att gcc gcc tac ctc tgc tcc agg gtg ccc ctg ccg tgc agg    1472
Val Thr Ile Ala Ala Tyr Leu Cys Ser Arg Val Pro Leu Pro Cys Arg
420                 425                 430                 435 agg aaa cct cgg gac tac acc atc aag gtg cac atg aac ctg ctg        1520
Arg Lys Pro Arg Asp Tyr Thr Ile Lys Val His Met Asn Leu Leu
                440                 445                 450 gcc gtc ttc ctg ctg gac acg agc ttc ctg ctc agc gag ccg gtg gcc    1568
Ala Val Phe Leu Leu Asp Thr Ser Phe Leu Leu Ser Glu Pro Val Ala
            455                 460                 465 ctg aca ggc tct gag gct ggc tgc cga gcc agt gcc atc ttc ctg cac    1616
Leu Thr Gly Ser Glu Ala Gly Cys Arg Ala Ser Ala Ile Phe Leu His
        470                 475                 480 ttc tcc ctg ctc acc tgc ctt tcc tgg atg ggc ctc gag ggg tac aac    1664
Phe Ser Leu Leu Thr Cys Leu Ser Trp Met Gly Leu Glu Gly Tyr Asn
    485                 490                 495 ctc tac cga ctc gtg gtg gag gtc ttt ggc acc tat gtc cct ggc tac    1712
Leu Tyr Arg Leu Val Val Glu Val Phe Gly Thr Tyr Val Pro Gly Tyr
500                 505                 510                 515 cta ctc aag ctg agc gcc atg ggc tgg ggc ttc ccc atc ttt ctg gtg    1760
Leu Leu Lys Leu Ser Ala Met Gly Trp Gly Phe Pro Ile Phe Leu Val
                520                 525                 530 acg ctg gtg gcc ctg gtg gat gtg gac aac tat ggc ccc atc atc ttg    1808
Thr Leu Val Ala Leu Val Asp Val Asp Asn Tyr Gly Pro Ile Ile Leu
            535                 540                 545 gct gtg cat agg act cca gag ggc gtc atc tac cct tcc atg tgc tgg    1856
Ala Val His Arg Thr Pro Glu Gly Val Ile Tyr Pro Ser Met Cys Trp
        550                 555                 560 atc cgg gac tcc ctg gtc agc tac atc acc aac ctg ggc ctc ttc agc    1904
Ile Arg Asp Ser Leu Val Ser Tyr Ile Thr Asn Leu Gly Leu Phe Ser
    565                 570                 575 ctg gtg ttt ctg ttc aac atg gcc atg cta gcc acc atg gtg gtg cag    1952
Leu Val Phe Leu Phe Asn Met Ala Met Leu Ala Thr Met Val Val Gln
580                 585                 590                 595 atc ctg cgg ctg cgc ccc cac acc caa aag tgg tca cat gtg ctg aca    2000
Ile Leu Arg Leu Arg Pro His Thr Gln Lys Trp Ser His Val Leu Thr
                600                 605                 610 ctg ctg ggc ctc agc ctg gtc ctt ggc ctg ccc tgg gcc ttg atc ttc    2048
Leu Leu Gly Leu Ser Leu Val Leu Gly Leu Pro Trp Ala Leu Ile Phe
            615                 620                 625 ttc tcc ttt gct tct ggc acc ttc cag ctt gtc gtc ctc tac ctt ttc    2096
Phe Ser Phe Ala Ser Gly Thr Phe Gln Leu Val Val Leu Tyr Leu Phe
        630                 635                 640 agc atc atc acc tcc ttc caa ggc ttc ctc atc ttc atc tgg tac tgg    2144
Ser Ile Ile Thr Ser Phe Gln Gly Phe Leu Ile Phe Ile Trp Tyr Trp
    645                 650                 655 tcc atg cgg ctg cag gcc cgg ggt ggc ccc tcc cct ctg aag agc aac    2192
Ser Met Arg Leu Gln Ala Arg Gly Gly Pro Ser Pro Leu Lys Ser Asn
660                 665                 670                 675 tca gac agc gcc agg ctc ccc atc agc tcg ggc agc acc tcg tcc agc    2240
Ser Asp Ser Ala Arg Leu Pro Ile Ser Ser Gly Ser Thr Ser Ser Ser
                680                 685                 690 cgc atc tag gcctccagcc cacctgccca tgtgatgaag cagagatgcg            2289
Arg Ile gcctcgtcgc acactgcctg tggccccccga gccaggccca gccccaggcc agtcagccgc    2349
agactttgga aagcccaacg accatggaga gatgggccgt tgccatggtg gacggactcc    2409
cgggctgggc ttttgaattg gccttgggga ctactcggct ctcactcagc tcccacggga    2469
ctcagaagtg cgccgccatg ctgcctaggg tactgtcccc acatctgtcc caacccagct    2529
```

-continued

```
ggaggcctgg tctctcctta caaaccctgg gcccagccct cattgctggg ggccaggcct    2589
tggatcttga gggtctggca catccttaat cctgtgcccc tgcctgggac agaaatgtgg    2649
ctccagttgc tctgtctctc gtggtcaccc tgagggcact ctgcatcctc tgtcattta    2709 acctcaggtg cacccaggg cgaatggggc ccagggcaga ccttcagggc cagagccctg    2769
gcggaggaga ggcccttgc caggagcaca gcagcagctc gcctacctct gagcccaggc    2829
cccctccctc cctcagcccc ccagtcctcc ctccatcttc cctggggttc tcctcctctc    2889
ccagggcctc cttgctcctt cgttcacagc tgggggtccc cgattccaat gctgtttttt    2949
ggggagtggt ttccaggagc tgcctggtgt ctgctgtaaa tgtttgtcta ctgcacaagc    3009
ctcggcctgc ccctgagcca ggctcggtac cgatgcgtgg gctgggctag gtccctctgt    3069
ccatctgggc ctttgtatga gctgcattgc ccttgctcac cctgaccaag cacacgcctc    3129
agaggggccc tcagcctctc ctgaagccct cttgtggcaa gaactgtgga ccatgccagt    3189
cccgtctggt ttccatccca ccactccaag gactgagact gacctcctct ggtgacactg    3249
gcctagagcc tgacactctc ctaagaggtt ctctccaagc ccccaaatag ctccaggcgc    3309
cctcggccgc ccatcatggt taattctgtc caacaaacac acacgggtag attgctggcc    3369
tgttgtaggt ggtagggaca cagatgaccg acctggtcac tcctcctgcc aacattcagt    3429
ctggtatgtg aggcgtgcgt gaagcaagaa ctcctggagc tacagggaca gggagccatc    3489
attcctgcct gggaatcctg gaagacttcc tgcaggagtc agcgttcaat cttgaccttg    3549
aagatgggaa ggatgttctt tttacgtacc aattctttg tcttttgata ttaaaaagaa    3609
gtacatgttc attgtagaga atttggaaac tgtagaagag aatcaagaag aaaaataaaa    3669
atcagctgtt gtaatcgcct agcaaaaaaa aaaaaaaaa aa                        3711
```

<210> SEQ ID NO 2
<211> LENGTH: 693
<212> TYPE: PRT
<213> ORGANISM: Homo sapiens

<400> SEQUENCE: 2

```
Met Thr Pro Gln Ser Leu Leu Gln Thr Thr Leu Phe Leu Leu Ser Leu
1               5                   10                  15

Leu Phe Leu Val Gln Gly Ala His Gly Arg Gly His Arg Glu Asp Phe
            20                  25                  30

Arg Phe Cys Ser Gln Arg Asn Gln Thr His Arg Ser Ser Leu His Tyr
        35                  40                  45

Lys Pro Thr Pro Asp Leu Arg Ile Ser Ile Glu Asn Ser Glu Glu Ala
    50                  55                  60

Leu Thr Val His Ala Pro Phe Pro Ala Ala His Pro Ala Ser Arg Ser
65                  70                  75                  80

Phe Pro Asp Pro Arg Gly Leu Tyr His Phe Cys Leu Tyr Trp Asn Arg
                85                  90                  95

His Ala Gly Arg Leu His Leu Leu Tyr Gly Lys Arg Asp Phe Leu Leu
            100                 105                 110

Ser Asp Lys Ala Ser Ser Leu Leu Cys Phe Gln His Gln Glu Glu Ser
        115                 120                 125

Leu Ala Gln Gly Pro Pro Leu Leu Ala Thr Ser Val Thr Ser Trp Trp
    130                 135                 140

Ser Pro Gln Asn Ile Ser Leu Pro Ser Ala Ala Ser Phe Thr Phe Ser
145                 150                 155                 160
```

-continued

```
Phe His Ser Pro Pro His Thr Ala Ala His Asn Ala Ser Val Asp Met
                165                 170                 175
Cys Glu Leu Lys Arg Asp Leu Gln Leu Leu Ser Gln Phe Leu Lys His
            180                 185                 190
Pro Gln Lys Ala Ser Arg Arg Pro Ser Ala Ala Pro Ala Ser Gln Gln
        195                 200                 205
Leu Gln Ser Leu Glu Ser Lys Leu Thr Ser Val Arg Phe Met Gly Asp
    210                 215                 220
Met Val Ser Phe Glu Glu Asp Arg Ile Asn Ala Thr Val Trp Lys Leu
225                 230                 235                 240
Gln Pro Thr Ala Gly Leu Gln Asp Leu His Ile His Ser Arg Gln Glu
                245                 250                 255
Glu Glu Gln Ser Glu Ile Met Glu Tyr Ser Val Leu Leu Pro Arg Thr
            260                 265                 270
Leu Phe Gln Arg Thr Lys Gly Arg Ser Gly Glu Ala Glu Lys Arg Leu
        275                 280                 285
Leu Leu Val Asp Phe Ser Ser Gln Ala Leu Phe Gln Asp Lys Asn Ser
    290                 295                 300
Ser His Val Leu Gly Glu Lys Val Leu Gly Ile Val Val Gln Asn Thr
305                 310                 315                 320
Lys Val Ala Asn Leu Thr Glu Pro Val Val Leu Thr Phe Gln His Gln
                325                 330                 335
Leu Gln Pro Lys Asn Val Thr Leu Gln Cys Val Phe Trp Val Glu Asp
            340                 345                 350
Pro Thr Leu Ser Ser Pro Gly His Trp Ser Ser Ala Gly Cys Glu Thr
        355                 360                 365
Val Arg Arg Glu Thr Gln Thr Ser Cys Phe Cys Asn His Leu Thr Tyr
    370                 375                 380
Phe Ala Val Leu Met Val Ser Ser Val Glu Val Asp Ala Val His Lys
385                 390                 395                 400
His Tyr Leu Ser Leu Leu Ser Tyr Val Gly Cys Val Val Ser Ala Leu
                405                 410                 415
Ala Cys Leu Val Thr Ile Ala Ala Tyr Leu Cys Ser Arg Val Pro Leu
            420                 425                 430
Pro Cys Arg Arg Lys Pro Arg Asp Tyr Thr Ile Lys Val His Met Asn
        435                 440                 445
Leu Leu Leu Ala Val Phe Leu Leu Asp Thr Ser Phe Leu Leu Ser Glu
    450                 455                 460
Pro Val Ala Leu Thr Gly Ser Glu Ala Gly Cys Arg Ala Ser Ala Ile
465                 470                 475                 480
Phe Leu His Phe Ser Leu Leu Thr Cys Leu Ser Trp Met Gly Leu Glu
                485                 490                 495
Gly Tyr Asn Leu Tyr Arg Leu Val Val Glu Val Phe Gly Thr Tyr Val
            500                 505                 510
Pro Gly Tyr Leu Leu Lys Leu Ser Ala Met Gly Trp Gly Phe Pro Ile
        515                 520                 525
Phe Leu Val Thr Leu Val Ala Leu Val Asp Val Asp Asn Tyr Gly Pro
    530                 535                 540
Ile Ile Leu Ala Val His Arg Thr Pro Glu Gly Val Ile Tyr Pro Ser
545                 550                 555                 560
Met Cys Trp Ile Arg Asp Ser Leu Val Ser Tyr Ile Thr Asn Leu Gly
                565                 570                 575
Leu Phe Ser Leu Val Phe Leu Phe Asn Met Ala Met Leu Ala Thr Met
```

-continued

```
            580                 585                 590
Val Val Gln Ile Leu Arg Leu Arg Pro His Thr Gln Lys Trp Ser His
        595                 600             605

Val Leu Thr Leu Leu Gly Leu Ser Leu Val Leu Gly Leu Pro Trp Ala
        610             615             620

Leu Ile Phe Phe Ser Phe Ala Ser Gly Thr Phe Gln Leu Val Val Leu
625             630             635                     640

Tyr Leu Phe Ser Ile Ile Thr Ser Phe Gln Gly Phe Leu Ile Phe Ile
                645             650                 655

Trp Tyr Trp Ser Met Arg Leu Gln Ala Arg Gly Gly Pro Ser Pro Leu
                660             665             670

Lys Ser Asn Ser Asp Ser Ala Arg Leu Pro Ile Ser Ser Gly Ser Thr
        675             680             685

Ser Ser Ser Arg Ile
        690
```

USE OF BIOMOLECULAR TARGETS IN THE TREATMENT AND VISUALIZATION OF TUMORS

BACKGROUND OF THE INVENTION

Among tumors, those of the brain are considered to have one of the least favorable prognoses for long term survival: the average life expectancy of an individual diagnosed with a central nervous system (CNS) tumor is just eight to twelve months. Several unique characteristics of both the brain and its particular types of neoplastic cells create daunting challenges for the complete treatment and management of brain tumors. Among these are the physical characteristics of the intracranial space; the relative biological isolation of the brain from the rest of the body; the relatively essential and irreplaceable nature of the organ mass; and the unique nature of brain tumor cells.

The intracranial space and physical layout of the brain create significant obstacles to treatment and recovery. The brain is primarily comprised of astrocytes, which make up the majority of the brain mass, and serve as a scaffold and support for the neurons, neurons, which carry the actual electrical impulses of the nervous system, and a minor contingent of other cells, such as insulating oligodendrocytes that produce myelin. These cell types give rise to primary brain tumors, including astrocytomas, neuroblastomas, glioblastomas, oligodendrogliomas, and the like.

The brain is encased in the rigid shell of the skull, and is cushioned by the cerebrospinal fluid. Because of the relatively small volume of the skull cavity, minor changes in the volume of tissue in the brain can dramatically increase intracranial pressure, causing damage to the entire organ. Thus, even small tumors can have a profound and adverse affect on the brain's function. The cramped physical location of the cranium also makes surgery and treatment of the brain a difficult and delicate procedure. However, because of the dangers of increased intracranial pressure from the tumor, surgery is often the first strategy of attack in treating brain tumors.

In addition to its physical isolation, the brain is chemically and biologically isolated from the rest of the body by the "Blood-Brain-Barrier" (or BBB). This physiological phenomenon is due to the "tightness" of the epithelial cell junctions in the lining of the blood vessels in the brain. Nutrients, which are actively transported across the cell lining, can reach the brain, but other molecules from the bloodstream are excluded. This prevents toxins, viruses, and other potentially dangerous molecules from entering the brain cavity. However, it also prevents therapeutic molecules, including many chemotherapeutic agents that are useful in other types of tumors, from crossing into the brain. Thus, many therapies directed at the brain must be delivered directly into the brain cavity, e.g. by an Ommaya reservoir, or administered in elevated dosages to ensure the diffusion of an effective amount across the BBB.

With the difficulties of administering chemotherapies to the brain, radiotherapy approaches have also been attempted. However, the amount of radiation necessary to completely destroy potential tumor-producing cells also produce unacceptable losses of healthy brain tissue. The retention of patient cognitive function while eliminating the tumor mass is another challenge to brain tumor treatment. Neoplastic brain cells are often pervasive, and travel throughout the entire brain mass. Thus, it is impossible to define a true "tumor margin," unlike, for example, in lung or bladder cancers. Unlike reproductive (ovarian, uterine, testicular, prostate, etc.), breast, kidney, or lung cancers, the entire organ, or even significant portions, cannot be removed to prevent the growth of new tumors. In addition, brain tumors are very heterogeneous, with different cell doubling times, treatment resistances, and other biochemical idiosyncrasies between the various cell populations that make up the tumor. This pervasive and variable nature greatly adds to the difficulty of treating brain tumors while preserving the health and function of normal brain tissue.

Although current surgical methods offer considerably better post-operative life for patients, current combination therapy methods (surgery, low-dosage radiation, and chemotherapy) have only improved the life expectancy of patients by one month, as compared to the methods of 30 years ago. Without effective agents to prevent the growth of brain tumor cells that are present outside the main tumor mass, the prognosis for these patients cannot be significantly improved. Although some immuno-affinity agents have been proposed and tested for the treatment of brain tumors, see, for example, the tenascin-targeting agents described in U.S. Pat. No. 5,624,659, these agents have not proven sufficient for the treatment of brain tumors. Thus, therapeutic agents which are directed towards new molecular targets, and are capable of specifically targeting and killing brain tumor cells, are urgently needed for the treatment of brain tumors.

Relevant Literature

Analysis of differential gene expression in glioblastoma may be found in, for example, Mariani et al. (2001) *J Neurooncol* 53(2):161-76; Markert et al. (2001) *Physiol Genomics* 5(1):21-33; Yano et al. (2000) *Neurol Res* 22(7): 650-6; Kroes et al. (2000) *Cancer Lett* 156(2):191-8; and Reis et al. (2000) *Am J Pathol* 156(2):425-32, among others.

SUMMARY OF THE INVENTION

The present invention provides methods and reagents for specifically targeting brain tumor neoplastic cells for both therapeutic and imaging purposes, by targeting the TM7XN1 protein, which has been identified as being overexpressed in brain tumors, thus allowing for the selective inhibition of cell function or selective marking for visualization with therapeutic or visualizing compositions that have a specific affinity for this target. The protein is also expressed in tissues from adenocarcinoma, non-melanoma, and renal carcinoma cells. The invention also provides methods for the identification of agents, e.g. small organic compounds, antibodies, etc. that modulate the expression of the TM7XN1 gene or the activity of the TM7XN1 gene product involved in such tumors, as well as methods for the treatment of disease by administering such agents to individuals suffering from such tumors.

BRIEF DESCRIPTION OF THE DRAWINGS

FIGS. 2A and 2B show the expression of TM7XN1 protein in in situ sections of glioblastoma tissue.

FIG. 4. Cell proliferation in response to TM7XN1 siRNA. Human glioblastoma derived cells were transfected with control siRNA. Cell proliferation was measured three days later. TM7XN1 siRNA transfected cells proliferated approximately 26% more slowly than control cells, indicating the role of TM7XN1 in tumor cell growth.

DETAILED DESCRIPTION OF THE EMBODIMENTS

Figure 1:
FIG. 1. Western blot analysis of human GBM derived cell lines and tissue. TM7XN1 is upregulated in several glioma cell lines and in GBM.
Figure 1:

The tumor target protein TM7XN1, and corresponding genetic sequence is differentially expressed between brain tumor tissue and normal brain tissue. The protein is also expressed in tissues from adenocarcinoma, non-melanoma, and renal carcinoma cells. Differential cloning between cancerous and normal brains has identified this brain tumor protein target gene by DNA sequence analysis. Genes and their protein products that are up-regulated in glioblastoma are important because they provide a specific marker for neoplastic cells, and are expected to mediate the initiation and progression of brain tumors. Inhibition of the gene and/or protein activity can be advantageous in treating brain tumors, e.g. glioblastoma multiforme; ependymoma; glioma; astrocytoma; medulloblastoma; neuroglioma; oligodendroglioma; meningioma, etc.

The overexpressed brain tumor protein target provides an excellent target for immunotherapeutic agents that either deliver cytotoxic agents to directly promote tumor cell death, or that alter the function of the brain tumor protein target to inhibit the normal physiology of the tumor cell. In one embodiment of the invention, a human or humanized antibody is provided, which specifically binds to the extracellular region of TM7XN1 with high affinity. Binding of the antibody to the extracellular region can lead to receptor down regulation or decreased biological activity, and decrease in cell proliferation, invasion and/or decrease in tumor size. In a preferred embodiment, an anti-TM7XN1 antibody binds to the extracellular domain of TM7XN1, where the extracellular domain comprises 1-401 amino acids of SEQ ID NO:2, or a fragment thereof.

Immunoimaging agents targeted to the brain tumor protein targets can be utilized to visualize the tumor mass in diagnostic methods, e.g. magnetic resonance imaging (MRI), radiography, etc. and/or in surgery, e.g. by the use of optically visible dye moieties in an immunoimaging agent, etc.

Therapeutic and prophylactic treatment methods for individuals suffering from, or at risk of a brain tumor, involve administering either a therapeutic or prophylactic amount of an agent that modulates the activity of TM7XN1 protein or gene, or specifically binds to TM7XN1 protein. For example, a chemotherapeutic agent can be coupled to a TM7XN1 specific binding moiety.

Screening methods may involve conducting various types of assays to identify agents that modulate the expression or activity of TM7XN1 gene or protein, or may involve screening for specific binding activity to TM7XN1 gene or protein. Lead compounds and/or binding moieties identified during these screens can serve as the basis for the synthesis of more active analogs. Lead compounds and/or active analogs generated therefrom can be formulated into pharmaceutical compositions effective in treating brain tumors.

G-protein-coupled receptors (GPCRs) constitute a vast protein family that encompass a wide range of functions (including various autocrine, paracrine, and endocrine processes). The sequences show considerable diversity at the sequence level, which diversity provides the basis for separation of the proteins into distinct groups. The main families of GPCRs include the rhodopsin-like GPCRs, the secretin-like GPCRs, the cAMP receptors, and the metabotropic glutamate receptor family.

Despite a similar 3D framework to other GPCRs, the secretin-like receptors have their own unique '7TM' signature. The GPCR TM7XN1 is a member of the secretin-like receptor family, which sequence is described by Fredriksson et al. (2002) *FEBS Lett.* 531(3):407-14; Liu et al. (1999) *Genomics* 55(3):296-305; and Zendman et al. (1999) *FEBS Lett.* 446(2-3):292-8. TM7XN1 diverges from other secretin-like family members, in that it has an extremely large N-terminal extracellular region (381 amino acids), and contains a novel cysteine box consisting of four cysteine residues, located just before the first transmembrane spanning domain. The rest of the amino-terminal domain contains a large number of possible N- and O-linked glycosylation sites similar to mucin-like proteins. These features suggest that it may play a role in cell-cell interactions. The short C-terminus contains some phosphorylation sites and a putative AMP binding domain (aa 675-686) which, together with a potential tyrosine kinase phosphorylation site (aa 546) between TM4 and TM5, may be indicative for interaction with signaling components.

Disease Conditions

The present methods are applicable to brain tumors, particularly glioblastoma. In general, the goals of brain tumor treatments are to remove as many tumor cells as possible, e.g. with surgery, kill as many of the cells left behind after surgery as possible with radiation and/or chemotherapy, and put remaining tumor cells into a nondividing, quiescent state for as long as possible with radiation and chemotherapy. Careful imaging surveillance is a crucial part of medical care, because tumor regrowth requires alteration of current treatment, or, for patients in the observation phase, restarting treatment.

Brain tumors are classified according to the kind of cell from which the tumor seems to originate. Diffuse, fibrillary astrocytomas are the most common type of primary brain tumor in adults. These tumors are divided histopathologically into three grades of malignancy: World Health Organization (WHO) grade II astrocytoma, WHO grade III anaplastic astrocytoma and WHO grade IV glioblastoma multiforme (GBM). WHO grade II astocytomas are the most indolent of the diffuse astrocytoma spectrum. Astrocytomas display a remarkable tendency to infiltrate the surrounding brain, confounding therapeutic attempts at local control. These invasive abilities are often apparent in low-grade as well as high-grade tumors.

Glioblastoma multiforme is the most malignant stage of astrocytoma, with survival times of less than 2 years for most patients. Histologically, these tumors are characterized by dense cellularity, high proliferation indices, endothelial proliferation and focal necrosis. The highly proliferative nature of these lesions likely results from multiple mitogenic effects. One of the hallmarks of GBM is endothelial proliferation. A host of angiogenic growth factors and their receptors are found in GBMs.

There are biologic subsets of astrocytomas, which may reflect the clinical heterogeneity observed in these tumors. These subsets include brain stem gliomas, which are a form of pediatric diffuse, fibrillary astrocytoma that often follow a malignant course. Brain stem GBMs share genetic features with those adult GBMs that affect younger patients. Pleomorphic xanthoastrocytoma (PXA) is a superficial, low-grade astrocytic tumor that predominantly affects young adults. While these tumors have a bizarre histological appearance, they are typically slow-growing tumors that may be amenable to surgical cure. Some PXAs, however, may recur as GBM. Pilocytic astrocytoma is the most common astrocytic tumor of childhood and differs clinically and histopathologically from the diffuse, fibrillary astrocytoma that affects adults. Pilocytic astrocytomas do not have the same genomic alterations as diffuse, fibrillary astrocytomas. Subependymal giant cell astrocytomas (SEGA) are periventricular, low-grade astrocytic tumors that are usually associated with tuberous sclerosis (TS), and are histologically identical to the so-called "candle-gutterings" that line the ventricles of TS patients. Similar to the other tumorous lesions in TS, these are slowly-growing and may be more akin to hamartomas than true neoplasms. Desmoplastic cerebral astrocytoma of infancy (DCAI) and desmoplastic infantile ganglioglioma (DIGG) are large, superficial, usually cystic, benign astrocytomas that affect children in the first year or two of life.

Oligodendrogliomas and oligoastrocytomas (mixed gliomas) are diffuse, usually cerebral tumors that are clinically and biologically most closely related to the diffuse, fibrillary astrocytomas. The tumors, however, are far less common than astrocytomas and have generally better prognoses than the diffuse astrocytomas. Oligodendrogliomas and oligoastrocytomas may progress, either to WHO grade III anaplastic oligodendroglioma or anaplastic oligoastrocytoma, or to WHO grade IV GBM. Thus, the genetic changes that lead to oligodendroglial tumors constitute yet another pathway to GBM.

Ependymomas are a clinically diverse group of gliomas that vary from aggressive intraventricular tumors of children to benign spinal cord tumors in adults. Transitions of ependymoma to GBM are rare. Choroid plexus tumors are also a varied group of tumors that preferentially occur in the ventricular system, ranging from aggressive supratentorial intraventricular tumors of children to benign cerebellopontine angle tumors of adults. Choroid plexus tumors have been reported occasionally in patients with Li-Fraumeni syndrome and von Hippel-Lindau (VHL) disease.

Medulloblastomas are highly malignant, primitive tumors that arise in the posterior fossa, primarily in children. Meningiomas are common intracranial tumors that arise in the meninges and compress the underlying brain. Meningiomas are usually benign, but some "atypical" meningiomas may recur locally, and some meningiomas are frankly malignant and may invade the brain or metastasize. Atypical and malignant meningiomas are not as common as benign meningiomas. Schwannomas are benign tumors that arise on peripheral nerves. Schwannomas may arise on cranial nerves, particularly the vestibular portion of the eighth cranial nerve (vestibular schwannomas, acoustic neuromas) where they present as cerebellopontine angle masses. Hemangioblastomas are tumors of uncertain origin that are composed of endothelial cells, pericytes and so-called stromal cells. These benign tumors most frequently occur in the cerebellum and spinal cord of young adults. Multiple hemangioblastomas are characteristic of von Hippel-Lindau disease (VHL). Hemangiopericytomas (HPCs) are dural tumors which may display locally aggressive behavior and may metastasize. The histogenesis of dural-based hemangiopericytoma (HPC) has long been debated, with some authors classifying it as a distinct entity and others classifying it as a subtype of meningioma.

The symptoms of both primary and metastatic brain tumors depend mainly on the location in the brain and the size of the tumor. Since each area of the brain is responsible for specific functions, the symptoms will vary a great deal. Tumors in the frontal lobe of the brain may cause weakness and paralysis, mood disturbances, difficulty in thinking, confusion and disorientation, and wide emotional mood swings. Parietal lobe tumors may cause seizures, numbness or paralysis, difficulty with handwriting, inability to perform simple mathematical problems, difficulty with certain movements, and loss of the sense of touch. Tumors in the occipital lobe can cause loss of vision in half of each visual field, visual hallucinations, and seizures. Temporal lobe tumors can cause seizures, perceptual and spatial disturbances, and receptive aphasia. If a tumor occurs in the cerebellum, the person may have ataxia, loss of coordination, headaches, and vomiting. Tumors in the hypothalamus may cause emotional changes, and changes in the perception of hot and cold. In addition, hypothalamic tumors may affect growth and nutrition in children. With the exception of the cerebellum, a tumor on one side of the brain causes symptoms and impairment on the opposite side of the body.

Other disorders of the nervous system that may be treated or imaged with the compositions of the present invention include, but are not limited to ischemic stroke, brain cancer, epilepsy, schizophrenia, depression, Alzheimer's Disease, Parkinson's Disease, Huntington's Chorea, traumatic head injury, dementia, coma, stupor, headache (and other neurological pain), vertigo, weakness, myasthenia gravis (and other disorders of the neuromuscular junction), ataxia and cerebellar disorders, cranial nerve disorders (such as Bell's Palsy), cerebrovascular disorders, infectious disorders including bacterial, fungal, viral and parasitic infections, multiple sclerosis, and other complications associated with pregnancy, medical illness, alcohol and substance abuse, toxins and metabolic deficiencies.

There are two major types of lung cancer: small cell and non-small cell, and different subtypes of non-small cell lung cancer. Each type grows and spreads in different ways, and is treated differently. Non-small cell is the most common form of lung cancer, growing and spreading more slowly than the small cell type, which is also known as oat cell cancer, due to its appearance under a microscope. Small cell lung cancer is more likely to spread to other organs in the body. About 40% percent of lung cancers are adenocarcinomas. Other adenocarcinomas include colon, ovarian, and endometrium cancers.

Renal cell carcinoma accounts for approximately 3% of adult malignancies and 90-95% of neoplasms arising from the kidney. It is also known as hypernephroma or clear cell carcinoma. Renal cell carcinoma is the most common tumor rising from the kidney, with about 30,000 cases per year diagnosed in the United States.

Nonmelanoma cell carcinomas are the second most common skin cancer. It includes basal and squamous cell carcinoma. In the US there are approximately 1 million cases per year of non-melanoma cancer. Squamous cell cancers may occur on all areas of the body including the mucous membranes, but are most common in areas exposed to the sun. Squamous cell carcinomas may also occur where skin has suffered certain kinds of injury: burns, scars, long-standing sores, sites previously exposed to X-rays or certain. In addition, chronic skin inflammation or medical conditions that suppress the immune system over an extended period of time may encourage development of squamous cell carcinoma. Cancers of the mouth, lips and palate fall into this category.

Identification of TM7XN1 as a Brain Tumor Target

The genetic sequence that comprises all or a part of a sequence encoding TM7XN1 is differentially expressed in brain tumor cells, particularly glioblastoma cells, relative to expression in normal, or non-disease conditions, and may be referred to as a "$T_{BT}$ gene", which encodes a "$T_{BT}$ protein". $T_{BT}$ genes were identified by creating subtracted and normalized cDNA libraries from glioblastoma tissues. The cDNAs from control and disease states were subjected to kinetic re-annealing hybridization during which normalization of transcript abundances and enrichment for low abundance transcripts occurs. Differential up- or down-regulated transcripts in tumors can be enriched by a subsequent "forward" or "reverse" subtraction step using a second driver cDNA as described in co-pending U.S. patent application Ser. No. 09/627,362, filed on Jul. 28, 2000. Only clones displaying a significant transcriptional induction and/or repression were sequenced and carried forward for expression profiling, using a variety of temporal, spatial and disease-related probe sets. Selected clones showing a significant transcriptional induction and/or repression were sequenced and functionally annotated in a proprietary database structure (See WO01/13105). Because large sequence fragments were utilized in the sequencing step, the data generated has a much higher fidelity and specificity than other approaches, such as SAGE. The resulting sequence information was compared to public databases using the BLAST (blastn) algorithm for DNA sequence comparisons and iterative-Smith Waterman analysis for protein sequence comparisons. The sequence of human TM7XN1 is provided herewith as SEQ ID NO:1 (nucleotide) and SEQ ID NO:2 (amino acid) sequences.

usually is one that is statistically significant, meaning that the probability of the difference occurring by chance (the P-value) is less than some predetermined level (e.g., 5%). Usually the confidence level (P value) is <0.05, more typically <0.01, and in other instances, <0.001.

Alternatively, the differentially expressed TM7XN1 gene may have its expression modulated, i.e., quantitatively increased or decreased, in normal versus diseased states, or under control versus experimental conditions. The difference in expression need only be large enough to be visualized via standard detection techniques as described above. Generally the difference in expression levels, measured by either the presence of mRNA or the protein product, will differ from basal levels (i.e. normal tissue) by at least about 2 fold, usually at least about 5 fold, and may be 10 fold, 100 fold, or more.

A sequence that has been identified as differentially expressed can be subjected to a functional validation process to determine whether the gene plays a role in tumor initiation, progression or maintenance. The term "functional validation" as used herein refers to a process whereby one determines whether modulation of expression or function of a candidate gene causes a detectable change in a cellular activity or cellular state for a reference cell, which can be a population of cells such as a tissue or an entire organism. The detectable change or alteration that is detected can be any activity carried out by the reference cell. Specific examples of activities or states in which alterations can be detected include, but are not limited to, phenotypic changes (e.g., cell morphology, cell proliferation, cell viability and cell death); cells acquiring resistance to a prior sensitivity or acquiring a sensitivity which previously did not exist; protein/protein interactions; cell movement; intracellular or

| AGY ID | DESCRIPTION | NUCLEOTIDE ACCESSION | SEQ ID | PROTEIN ACCESSION | SEQ ID | ADDITIONAL ACCESSIONS |
|---|---|---|---|---|---|---|
| AL00003_CP1_J03 | Homo sapiens G protein-coupled receptor 56 (GPR56) | NM_005682 | 1 | NP_005673 | 2 | AJ011001, XM_007954 |

The Genbank entry accession number XM_007954, which formerly referred to the TM7XN1/GPR56 sequence, has been removed from NCBI and replaced with the new accession, NM_005682. The "Additional Accessions" column represents additional nucleotide sequences with updated descriptions and identical homology.

"Differential expression" as used herein refers to both quantitative as well as qualitative differences in the genes' temporal and/or tissue expression patterns. Thus, the differentially expressed TM7XN1 gene may have its expression activated or inactivated in normal versus diseased conditions, or in control versus experimental conditions. Such a qualitatively regulated gene will exhibit an expression pattern within a given tissue or cell type that is detectable in either control or tumor samples, but is not detectable in both. Detectable, as used herein, refers to an RNA expression pattern that is detectable via the standard techniques of differential display, reverse transcription-(RT-) PCR and/or Northern analyses, which are well known to those of skill in the art. Generally, differential expression means that there is at least a 20% change, and in other instances at least a 2-, 3-, 5- or 10-fold difference between disease and control tissue expression, e.g. with non-neuronal tissues. The difference intercellular signaling; cell/cell interactions; cell activation (e.g., T cell activation, B cell activation, mast cell degranulation); release of cellular components (e.g., hormones, chemokines and the like); and metabolic or catabolic reactions.

A variety of options are available for functionally validating candidate genes. For example, a number of options are available to detect interference of candidate gene expression (i.e., to detect candidate gene silencing). In general, inhibition in expression is detected by detecting a decrease in the level of the protein encoded by the candidate gene, determining the level of mRNA transcribed from the gene and/or detecting a change in phenotype associated with candidate gene expression.

Such methods as RNAi technology can be used. Antisense technology can also be utilized to functionally validate a candidate gene. In this approach, an antisense polynucleotide that specifically hybridizes to a segment of the coding sequence for the candidate gene is administered to inhibit expression of the candidate gene in those cells into which it is introduced. The functional role that a candidate gene plays in a cell can also be assessed using gene "knockout" approaches in which the candidate gene is deleted, modified, or inhibited on either a single or both alleles. The cells or animals can be optionally be reconstituted with a wild-type candidate gene as part of a further analysis.

In one embodiment of the invention, RNAi technology is used in functional validation. As used herein, RNAi technology refers to a process in which double-stranded RNA is introduced into cells expressing a candidate gene to inhibit expression of the candidate gene, i.e., to "silence" its expression. The dsRNA is selected to have substantial identity with the candidate gene. In general such methods initially involve transcribing a nucleic acids containing all or part of a candidate gene into single- or double-stranded RNA. Sense and anti-sense RNA strands are allowed to anneal under appropriate conditions to form dsRNA. The resulting dsRNA is introduced into reference cells via various methods and the degree of attenuation in expression of the candidate gene is measured using various techniques. Usually one detects whether inhibition alters a cellular state or cellular activity.

Nucleic Acids

The TM7XN1 nucleic acids sequences find use in diagnostic and therapeutic methods, for the recombinant production of the encoded polypeptide, and the like. The nucleic acids of the invention include nucleic acids having a high degree of sequence similarity or sequence identity to SEQ ID NO:1. Sequence identity can be determined by hybridization under stringent conditions, for example, at 50° C. or higher and 0.1×SSC (9 mM NaCl/0.9 mM Na citrate). Hybridization methods and conditions are well known in the art, see, e.g., U.S. Pat. No. 5,707,829. Nucleic acids that are substantially identical to the provided nucleic acid sequence, e.g. allelic variants, genetically altered versions of the gene, splice variants etc., bind to one of the sequences provided in Table 1 under stringent hybridization conditions. Further specific guidance regarding the preparation of nucleic acids is provided by Fleury et al. (1997) *Nature Genetics* 15:269-272; Tartaglia et al., PCT Publication No. WO 96/05861; and Chen et al., PCT Publication No. WO 00/06087, each of which is incorporated herein in its entirety.

The TM7XN1 sequence may be obtained using various methods well known to those skilled in the art, including but not limited to the use of appropriate probes to detect the gene within an appropriate cDNA or genomic DNA library, antibody screening of expression libraries to detect cloned DNA fragments with shared structural features, direct chemical synthesis, and amplification protocols. Libraries are preferably prepared from cells or tissues of normal brains or brain tumors. Cloning methods are described in Berger and Kimmel, Guide to Molecular Cloning Techniques, Methods in Enzymology, 152, Academic Press, Inc. San Diego, Calif.; Sambrook, et al. (1989) Molecular Cloning—A Laboratory Manual (2nd ed) Vols. 1-3, Cold Spring Harbor Laboratory, Cold Spring Harbor Press, NY; and Current Protocols (1994), a joint venture between Greene Publishing Associates, Inc. and John Wiley and Sons, Inc.

The sequence obtained from clones containing partial coding sequences or non-coding sequences can be used to obtain the entire coding region by using the RACE method (Chenchik et al. (1995) CLONTECHniques (X) 1: 5-8). Oligonucleotides can be designed from the partial clone's analyzed sequence and subsequently utilized to amplify a reverse transcribed mRNA encoding the entire coding sequence. Alternatively, probes can be used to screen cDNA libraries prepared from an appropriate cell or cell line in which the gene is transcribed. Once the target nucleic acid is identified, it can be isolated and cloned using well-known amplification techniques. Such techniques include, the polymerase chain reaction (PCR) the ligase chain reaction (LCR), Qβ-replicase amplification, the self-sustained sequence replication system (SSR) and the transcription based amplification system (TAS). Such methods include, those described, for example, in U.S. Pat. No. 4,683,202 to Mullis et al.; PCR Protocols A Guide to Methods and Applications (Innis et al. eds) Academic Press Inc. San Diego, Calif. (1990); Kwoh et al. (1989) Proc. Natl. Acad. Sci. USA 86: 1173; Guatelli et al. (1990) Proc. Natl. Acad. Sci. USA 87: 1874; Lomell et al. (1989) J. Clin. Chem. 35: 1826; Landegren et al. (1988) Science 241: 1077-1080; Van Brunt (1990) Biotechnology 8: 291-294; Wu and Wallace (1989) Gene 4: 560; and Barringer et al. (1990) Gene 89: 117.

As an alternative to cloning a nucleic acid, a suitable nucleic acid can be chemically synthesized. Direct chemical synthesis methods include, for example, the phosphotriester method of Narang et al. (1979) Meth. Enzymol. 68: 90-99; the phosphodiester method of Brown et al. (1979) Meth. Enzymol. 68: 109-151; the diethylphosphoramidite method of Beaucage et al. (1981) Tetra. Lett., 22: 1859-1862; and the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. While chemical synthesis of DNA is often limited to sequences of about 100 bases, longer sequences can be obtained by the ligation of shorter sequences. Alternatively, subsequences may be cloned and the appropriate subsequences cleaved using appropriate restriction enzymes.

The nucleic acid can be cDNAs or genomic DNAs, as well as fragments thereof. The term "cDNA" as used herein is intended to include all nucleic acids that share the arrangement of sequence elements found in native mature mRNA species, where sequence elements are exons and 3' and 5' non-coding regions. Normally mRNA species have contiguous exons, with the intervening introns, when present, being removed by nuclear RNA splicing, to create a continuous open reading frame encoding a polypeptide of the invention.

A genomic sequence of interest comprises the nucleic acid present between the initiation codon and the stop codon, as defined in the listed sequences, including all of the introns that are normally present in a native chromosome. It can further include the 3' and 5' untranslated regions found in the mature mRNA. It can further include specific transcriptional and translational regulatory sequences, such as promoters, enhancers, etc., including about 1 kb, but possibly more, of flanking genomic DNA at either the 5' or 3' end of the transcribed region. The genomic DNA flanking the coding region, either 3' or 5', or internal regulatory sequences as sometimes found in introns, contains sequences required for proper tissue, stage-specific, or disease-state specific expression, and are useful for investigating the up-regulation of expression in tumor cells.

Probes specific to the nucleic acid of the invention can be generated using the nucleic acid sequence disclosed in the seqlist. The probes are preferably at least about 18 nt, 25 nt, 50 nt or more of the corresponding contiguous sequence of one of the sequences provided in the seqlist, and are usually less than about 2, 1, or 0.5 kb in length. Preferably, probes are designed based on a contiguous sequence that remains unmasked following application of a masking program for masking low complexity. Double or single stranded fragments can be obtained from the DNA sequence by chemically synthesizing oligonucleotides in accordance with conventional methods, by restriction enzyme digestion, by PCR amplification, etc. The probes can be labeled, for example, with a radioactive, biotinylated, or fluorescent tag.

The nucleic acids of the subject invention are isolated and obtained in substantial purity, generally as other than an intact chromosome. Usually, the nucleic acids, either as DNA or RNA, will be obtained substantially free of other naturally-occurring nucleic acid sequences, generally being at least about 50%, usually at least about 90% pure and are typically "recombinant," e.g., flanked by one or more nucleotides with which it is not normally associated on a naturally occurring chromosome.

The nucleic acids of the invention can be provided as a linear molecule or within a circular molecule, and can be provided within autonomously replicating molecules (vectors) or within molecules without replication sequences. Expression of the nucleic acids can be regulated by their own or by other regulatory sequences known in the art. The nucleic acids of the invention can be introduced into suitable host cells using a variety of techniques available in the art, such as transferrin polycation-mediated DNA transfer, transfection with naked or encapsulated nucleic acids, liposome-mediated DNA transfer, intracellular transportation of DNA-coated latex beads, protoplast fusion, viral infection, electroporation, gene gun, calcium phosphate-mediated transfection, and the like.

For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other. For hybridization probes, it may be desirable to use nucleic acid analogs, in order to improve the stability and binding affinity. The term "nucleic acid" shall be understood to encompass such analogs.

Polypeptides

TM7XN1 polypeptides are of interest for screening methods, as reagents to raise antibodies, as therapeutics, and the like. Such polypeptides can be produced through isolation from natural sources, recombinant methods and chemical synthesis. In addition, functionally equivalent polypeptides may find use, where the equivalent polypeptide may contain deletions, additions or substitutions of amino acid residues that result in a silent change, thus producing a functionally equivalent differentially expressed on pathway gene product. Amino acid substitutions may be made on the basis of similarity in polarity, charge, solubility, hydrophobicity, hydrophilicity, and/or the amphipathic nature of the residues involved. "Functionally equivalent", as used herein, refers to a protein capable of exhibiting a substantially similar in vivo activity as the polypeptide encoded by an ischemia associated gene, as provided in The seqlist.

The polypeptides may be produced by recombinant DNA technology using techniques well known in the art. Methods which are well known to those skilled in the art can be used to construct expression vectors containing coding sequences and appropriate transcriptional/translational control signals. These methods include, for example, in vitro recombinant DNA techniques, synthetic techniques and in vivo recombination/genetic recombination. Alternatively, RNA capable of encoding the polypeptides of interest may be chemically synthesized.

Typically, the coding sequence is placed under the control of a promoter that is functional in the desired host cell to produce relatively large quantities of the gene product. An extremely wide variety of promoters are well-known, and can be used in the expression vectors of the invention, depending on the particular application. Ordinarily, the promoter selected depends upon the cell in which the promoter is to be active. Other expression control sequences such as ribosome binding sites, transcription termination sites and the like are also optionally included. Constructs that include one or more of these control sequences are termed "expression cassettes." Expression can be achieved in prokaryotic and eukaryotic cells utilizing promoters and other regulatory agents appropriate for the particular host cell. Exemplary host cells include, but are not limited to, E. coli, other bacterial hosts, yeast, and various higher eukaryotic cells such as the COS, CHO and HeLa cells lines and myeloma cell lines.

In mammalian host cells, a number of viral-based expression systems may be used, including retrovirus, lentivirus, adenovirus, adeno-associated virus, and the like. In cases where an adenovirus is used as an expression vector, the coding sequence of interest can be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing differentially expressed or pathway gene protein in infected hosts.

Specific initiation signals may also be required for efficient translation of the genes. These signals include the ATG initiation codon and adjacent sequences. In cases where a complete gene, including its own initiation codon and adjacent sequences, is inserted into the appropriate expression vector, no additional translational control signals may be needed. However, in cases where only a portion of the gene coding sequence is inserted, exogenous translational control signals must be provided. These exogenous translational control signals and initiation codons can be of a variety of origins, both natural and synthetic. The efficiency of expression may be enhanced by the inclusion of appropriate transcription enhancer elements, transcription terminators, etc.

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, WI38, etc.

For long-term, high-yield production of recombinant proteins, stable expression is preferred. For example, cell lines that stably express the differentially expressed or pathway gene protein may be engineered. Rather than using expression vectors that contain viral origins of replication, host cells can be transformed with DNA controlled by appropriate expression control elements, and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines that express the target protein. Such engineered cell lines may be particularly useful in screening and evaluation of compounds that affect the endogenous activity of the $T_{BT}$ protein. A number of selection systems may be used, including but not limited to the herpes simplex virus thymidine kinase, hypoxanthine-guanine phosphoribosyltransferase, and adenine phosphoribosyltransferase genes. Antimetabolite resistance can be used as the basis of selection for dhfr, which confers resistance to methotrexate; gpt, which confers resistance to mycophenolic acid; neo, which confers resistance to the aminoglycoside G-418; and hygro, which confers resistance to hygromycin.

The polypeptide may be labeled, either directly or indirectly. Any of a variety of suitable labeling systems may be used, including but not limited to, radioisotopes such as $^{125}I$; enzyme labeling systems that generate a detectable colorimetric signal or light when exposed to substrate; and fluorescent labels. Indirect labeling involves the use of a protein, such as a labeled antibody, that specifically binds to the polypeptide of interest. Such antibodies include but are not limited to polyclonal, monoclonal, chimeric, single chain, Fab fragments and fragments produced by a Fab expression library.

Once expressed, the recombinant polypeptides can be purified according to standard procedures of the art, including ammonium sulfate precipitation, affinity columns, ion exchange and/or size exclusivity chromatography, gel electrophoresis and the like (see, generally, R. Scopes, Protein Purification, Springer-Verlag, N.Y. (1982), Deutscher, Methods in Enzymology Vol. 182: Guide to Protein Purification., Academic Press, Inc. N.Y. (1990)).

As an option to recombinant methods, polypeptides and oligopeptides can be chemically synthesized. Such methods typically include solid-state approaches, but can also utilize solution based chemistries and combinations or combinations of solid-state and solution approaches. Examples of solid-state methodologies for synthesizing proteins are described by Merrifield (1964) J. Am. Chem. Soc. 85:2149; and Houghton (1985) Proc. Natl. Acad. Sci., 82:5132. Fragments of a $T_{BT}$ protein can be synthesized and then joined together. Methods for conducting such reactions are described by Grant (1992) Synthetic Peptides: A User Guide, W. H. Freeman and Co., N.Y.; and in "Principles of Peptide Synthesis," (Bodansky and Trost, ed.), Springer-Verlag, Inc. N.Y., (1993).

For various purposes, for example as an immunogen, the entire $T_{BT}$ polypeptide or a fragment derived therefrom may be used. Preferably, one or more 8-30 amino acid peptide portions, e.g. of an extracellular domain may be utilized, with peptides in the range of 10-20 being a more economical choice. Custom-synthesized peptides in this range are available from a multitude of vendors, and can be order conjugated to KLH or BSA. Alternatively, peptides in excess of 30 amino acids may be synthesized by solid-phase methods, or may be recombinantly produced in a suitable recombinant protein production system. In order to ensure proper protein glycosylation and processing, an animal cell system (e.g., Sf9 or other insect cells, CHO or other mammalian cells) is preferred. A $T_{BT}$ polypeptide may be used as a cancer vaccine, as described below.

Specific Binding Members

The term "specific binding member" or "binding member" as used herein refers to a member of a specific binding pair, i.e. two molecules, usually two different molecules, where one of the molecules (i.e., first specific binding member) through chemical or physical means specifically binds to the other molecule (i.e., second specific binding member). The complementary members of a specific binding pair are sometimes referred to as a ligand and receptor; or receptor and counter-receptor. For the purposes of the present invention, the two binding members may be known to associate with each other, for example where an assay is directed at detecting compounds that interfere with the association of a known binding pair. Alternatively, candidate compounds suspected of being a binding partner to a compound of interest may be used.

Specific binding pairs of interest include carbohydrates and lectins; complementary nucleotide sequences; peptide ligands and receptor; effector and receptor molecules; hormones and hormone binding protein; enzyme cofactors and enzymes; enzyme inhibitors and enzymes; lipid and lipid-binding protein; etc. The specific binding pairs may include analogs, derivatives and fragments of the original specific binding member. For example, a receptor and ligand pair may include peptide fragments, chemically synthesized peptidomimetics, labeled protein, derivatized protein, etc.

In a preferred embodiment, the specific binding member is an antibody. The term "antibody" or "antibody moiety" is intended to include any polypeptide chain-containing molecular structure with a specific shape that fits to and recognizes an epitope, where one or more non-covalent binding interactions stabilize the complex between the molecular structure and the epitope. The term includes monoclonal antibodies, multispecific antibodies (antibodies that include more than one domain specificity), human antibody, humanized antibody, and antibody fragments with the desired biological activity.

Antibodies that bind specifically to one of the brain tumor protein targets are referred to as anti-TM7XN1 antibodies, or α(TBT). The specific or selective fit of a given structure and its specific epitope is sometimes referred to as a "lock and key" fit. The archetypal antibody molecule is the immunoglobulin, and all types of immunoglobulins, IgG, e.g. IgG1, IgG2a, IgG2b, IgG3, IgG4, IgM, IgA, IgE, IgD, etc., from all sources, e.g. human, rodent, rabbit, cow, sheep, pig, dog, other mammal, chicken, other avians, etc., are considered to be "antibodies." Antibodies utilized in the present invention may be polyclonal antibodies, although monoclonal antibodies are preferred because they may be reproduced by cell culture or recombinantly, and can be modified to reduce their antigenicity.

Polyclonal antibodies can be raised by a standard protocol by injecting a production animal with an antigenic composition, formulated as described above. See, e.g., Harlow and Lane, Antibodies: A Laboratory Manual, Cold Spring Harbor Laboratory, 1988. In one such technique, a TM7XN1 antigen comprising an antigenic portion of the polypeptide is initially injected into any of a wide variety of mammals (e.g., mice, rats, rabbits, sheep or goats). When utilizing an entire protein, or a larger section of the protein, antibodies may be raised by immunizing the production animal with the protein and a suitable adjuvant (e.g., Fruend's, Fruend's complete, oil-in-water emulsions, etc.) When a smaller peptide is utilized, it is advantageous to conjugate the peptide with a larger molecule to make an immunostimulatory conjugate. Commonly utilized conjugate proteins that are commercially available for such use include bovine serum albumin (BSA) and keyhole limpet hemocyanin (KLH). In order to raise antibodies to particular epitopes, peptides derived from the full sequence may be utilized. Alternatively, in order to generate antibodies to relatively short peptide portions of the brain tumor protein target, a superior immune response may be elicited if the polypeptide is joined to a carrier protein, such as ovalbumin, BSA or KLH. The peptide-conjugate is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Alternatively, for monoclonal antibodies, hybridomas may be formed by isolating the stimulated immune cells, such as those from the spleen of the inoculated animal. These cells are then fused to immortalized cells, such as myeloma cells or transformed cells, which are capable of replicating indefinitely in cell culture, thereby producing an immortal, immunoglobulin-secreting cell line. The immortal cell line utilized is preferably selected to be deficient in enzymes necessary for the utilization of certain nutrients. Many such cell lines (such as myelomas) are known to those skilled in the art, and include, for example: thymidine kinase (TK) or hypoxanthine-guanine phosphoriboxyl transferase (HGPRT). These deficiencies allow selection for fused cells according to their ability to grow on, for example, hypoxanthine aminopterinthymidine medium (HAT).

Preferably, the immortal fusion partners utilized are derived from a line that does not secrete immunoglobulin. The resulting fused cells, or hybridomas, are cultured under conditions that allow for the survival of fused, but not unfused, cells and the resulting colonies screened for the production of the desired monoclonal antibodies. Colonies producing such antibodies are cloned, expanded, and grown so as to produce large quantities of antibody, see Kohler and Milstein, 1975 Nature 256:495 (the disclosures of which are hereby incorporated by reference).

Large quantities of monoclonal antibodies from the secreting hybridomas may then be produced by injecting the clones into the peritoneal cavity of mice and harvesting the ascites fluid therefrom. The mice, preferably primed with pristane, or some other tumor-promoter, and immunosuppressed chemically or by irradiation, may be any of various suitable strains known to those in the art. The ascites fluid is harvested from the mice and the monoclonal antibody purified therefrom, for example, by CM Sepharose column or other chromatographic means. Alternatively, the hybridomas may be cultured in vitro or as suspension cultures. Batch, continuous culture, or other suitable culture processes may be utilized. Monoclonal antibodies are then recovered from the culture medium or supernatant.

In addition, the antibodies or antigen binding fragments may be produced by genetic engineering. In this technique, as with the standard hybridoma procedure, antibody-producing cells are sensitized to the desired antigen or immunogen. The messenger RNA isolated from the immune spleen cells or hybridomas is used as a template to make cDNA using PCR amplification. A library of vectors, each containing one heavy chain gene and one light chain gene retaining the initial antigen specificity, is produced by insertion of appropriate sections of the amplified immunoglobulin cDNA into the expression vectors. A combinatorial library is constructed by combining the heavy chain gene library with the light chain gene library. This results in a library of clones which co-express a heavy and light chain (resembling the Fab fragment or antigen binding fragment of an antibody molecule). The vectors that carry these genes are co-transfected into a host (e.g. bacteria, insect cells, mammalian cells, or other suitable protein production host cell.). When antibody gene synthesis is induced in the transfected host, the heavy and light chain proteins self-assemble to produce active antibodies that can be detected by screening with the antigen or immunogen.

Preferably, recombinant antibodies are produced in a recombinant protein production system that correctly glycosylates and processes the immunoglobulin chains, such as insect or mammalian cells. An advantage to using insect cells, which utilize recombinant baculoviruses for the production of antibodies, is that the baculovirus system allows production of mutant antibodies much more rapidly than stably transfected mammalian cell lines. In addition, insect cells have been shown to correctly process and glycosylate eukaryotic proteins, which prokaryotic cells do not. Finally, the baculovirus expression of foreign protein has been shown to constitute as much as 50-75% of the total cellular protein late in viral infection, making this system an excellent means of producing milligram quantities of the recombinant antibodies.

Antibodies with a reduced propensity to induce a violent or detrimental immune response in humans (such as anaphylactic shock), and which also exhibit a reduced propensity for priming an immune response which would prevent repeated dosage with the antibody therapeutic or imaging agent are preferred for use in the invention. Even through the brain is relatively isolated behind the blood brain barrier, an immune response still can occur in the form of increased leukocyte infiltration, and inflammation. Although some increased immune response against the tumor is desirable, the concurrent binding and inactivation of the therapeutic or imaging agent generally outweighs this benefit. Thus, humanized, single chain, chimeric, or human antibodies, which produce less of an immune response when administered to humans, are preferred for use in the present invention. Also included in the invention are multi-domain antibodies, and anti-idiotypic antibodies that "mimic" TM7XN1. For example, antibodies that bind to a Tm7XN1 domain and competitively inhibit the binding of Tm7XN1 to its ligand may be used to generate anti-idiotypes that "mimic" TM7XN1 and, therefore, bind, activate, or neutralize Tm7XN1, TM7XN1 ligand, TM7XN1 receptor, or TM7XN1 ligand. Such anti-idiotypic antibodies or Fab fragments of such anti-idiotypes can be used in therapeutic regimens involving a TM7XN1 mediated pathway (see, for example, Greenspan and Bona (1993) *FASEB J* 7(5):437-444; Nissinoff (1991) *J. Immunol.* 147(8):2429-2438.

A chimeric antibody is a molecule in which different portions are derived from different animal species, for example those having a variable region derived from a murine mAb and a human immunoglobulin constant region. Techniques for the development of chimeric antibodies are described in the literature. See, for example, Morrison et al. (1984) *Proc. Natl. Acad. Sci.* 81:6851-6855; Neuberger et al. (1984) *Nature* 312:604-608; Takeda et al. (1985) *Nature* 314:452-454. Single chain antibodies are formed by linking the heavy and light chain fragments of the Fv region via an amino acid bridge, resulting in a single chain polypeptide. See, for example, Huston et al., Science 242:423-426; Proc. Natl. Acad. Sci. 85:5879-5883; and Ward et al. *Nature* 341:544-546.

Antibody fragments that recognize specific epitopes may be generated by techniques well known in the field. These fragments include, without limitation, $F(ab')_2$ fragments, which can be produced by pepsin digestion of the antibody molecule, and Fab fragments, which can be generated by reducing the disulfide bridges of the $F(ab')_2$ fragments.

In one embodiment of the invention, a human or humanized antibody is provided, which specifically binds to the extracellular region of TM7XN1 with high affinity. Binding of the antibody to the extracellular region can lead to receptor down regulation or decreased biological activity, and decrease in cell proliferation, invasion and/or decrease in tumor size. Low affinity binders may also be useful for some immuno-therapies. See Lonberg et al. (1994) *Nature* 368:856-859; and Lonberg and Huszar (1995) Internal Review of Immunology 13:65-93. In another aspect of the invention, a humanized antibody is provided that specifically binds to the extracellular region of TM7XN1 with high affinity, and which bears resemblance to the human antibody. These antibodies resemble human antibodies and thus can be administered to a human patient with minimal negative side effects.

Humanized antibodies are human forms of non-human antibodies. They are chimeras with a minimum sequence derived from of non-human Immunoglobulin. To overcome the intrinsic undesirable properties of murine monoclonal antibodies, recombinant murine antibodies engineered to incorporate regions of human antibodies, also called "humanized antibodies" are being developed. This alternative strategy was adopted as it is difficult to generate human antibodies directed to human antigens such as cell surface molecules. A humanized antibody contains complementarity determining region (CDR) regions and a few other amino acid of a murine antibody while the rest of the antibody is of human origin.

In a preferred embodiment, an anti-TM7XN1 antibody binds to the extracellular domain of TM7XN1, where the extracellular domain comprises 1-401 amino acids of SEQ ID NO:2, or a fragment thereof, particularly an epitopic fragment of at least about 4 amino acids, usually at least about 8 amino acids, and may be 20 amino acids or longer, for example where the antibody binds to a three-dimensional peptide structure comprising non-contiguous residues. The antibody may bind, activate, neutralize, inhibit or function as a protein blocker. It may prevent interaction with another ligand.

Antibodies of interest may prevent cleavage at the GPS domain. This domain has sequence similarity to a cleavage site in latrophilin, between Leu and Thr residues that are conserved in certain receptors.

Chimeric antibodies may be made by recombinant means by combining the murine variable light and heavy chain regions (VK and VH), obtained from a murine (or other animal-derived) hybridoma clone, with the human constant light and heavy chain regions, in order to produce an antibody with predominantly human domains. The production of such chimeric antibodies is well known in the art, and may be achieved by standard means (as described, e.g., in U.S. Pat. No. 5,624,659, incorporated fully herein by reference). Humanized antibodies are engineered to contain even more human-like immunoglobulin domains, and incorporate only the complementarity-determining regions of the animal-derived antibody. This is accomplished by carefully examining the sequence of the hyper-variable loops of the variable regions of the monoclonal antibody, and fitting them to the structure of the human antibody chains. Although facially complex, the process is straightforward in practice. See, e.g., U.S. Pat. No. 6,187,287, incorporated fully herein by reference.

Alternatively, polyclonal or monoclonal antibodies may be produced from animals that have been genetically altered to produce human immunoglobulins. Techniques for generating such animals, and deriving antibodies therefrom, are described in U.S. Pat. Nos. 6,162,963 and 6,150,584, incorporated fully herein by reference.

Alternatively, single chain antibodies (Fv, as described below) can be produced from phage libraries containing human variable regions. See U.S. Pat. No. 6,174,708. Intrathecal administration of single-chain immunotoxin, LMB-7 [B3(Fv)-PE38], has been shown to cure of carcinomatous meningitis in a rat model. *Proc Natl. Acad. Sci USA* 92, 2765-9, all of which are incorporated by reference fully herein.

In addition to entire immunoglobulins (or their recombinant counterparts), immunoglobulin fragments comprising the epitope binding site (e.g., Fab', $F(ab')_2$, or other fragments) are useful as antibody moieties in the present invention. Such antibody fragments may be generated from whole immunoglobulins by ficin, pepsin, papain, or other protease cleavage. "Fragment," or minimal immunoglobulins may be designed utilizing recombinant immunoglobulin techniques. For instance "Fv" immunoglobulins for use in the present invention may be produced by linking a variable light chain region to a variable heavy chain region via a peptide linker (e.g., poly-glycine or another sequence which does not form an alpha helix or beta sheet motif).

Fv fragments are heterodimers of the variable heavy chain domain ($V_H$) and the variable light chain domain ($V_L$). The heterodimers of heavy and light chain domains that occur in whole IgG, for example, are connected by a disulfide bond. Recombinant Fvs in which $V_H$ and $V_L$ are connected by a peptide linker are typically stable, see, for example, Huston et al., Proc. Natl. Acad, Sci. USA 85:5879-5883 (1988) and Bird et al., Science 242:423-426 (1988), both fully incorporated herein, by reference. These are single chain Fvs which have been found to retain specificity and affinity and have been shown to be useful for imaging tumors and to make recombinant immunotoxins for tumor therapy. However, researchers have bound that some of the single chain Fvs have a reduced affinity for antigen and the peptide linker can interfere with binding. Improved Fv's have been also been made which comprise stabilizing disulfide bonds between the $V_H$ and $V_L$ regions, as described in U.S. Pat. No. 6,147,203, incorporated fully herein by reference. Any of these minimal antibodies may be utilized in the present invention, and those which are humanized to avoid HAMA reactions are preferred for use in embodiments of the invention.

In addition, derivatized immunoglobulins with added chemical linkers, detectable moieties, such as fluorescent dyes, enzymes, substrates, chemiluminescent moieties and the like, or specific binding moieties, such as streptavidin, avidin, or biotin, and the like may be utilized in the methods and compositions of the present invention. For convenience, the term "antibody" or "antibody moiety" will be used throughout to generally refer to molecules which specifically bind to an epitope of the brain tumor protein targets, although the term will encompass all immunoglobulins, derivatives, fragments, recombinant or engineered immunoglobulins, and modified immunoglobulins, as described above.

Candidate anti-TM7XN1 antibodies can be tested for by any suitable standard means, e.g. ELISA assays, etc. As a first screen, the antibodies may be tested for binding against the immunogen, or against the entire brain tumor protein target extracellular domain or protein. As a second screen, anti-TM7XN1 candidates may be tested for binding to an appropriate tumor cell line, or to primary tumor tissue samples. For these screens, the anti-TM7XN1 candidate antibody may be labeled for detection. After selective binding to the brain tumor protein target is established, the candidate antibody, or an antibody conjugate produced as described below, may be tested for appropriate activity (i.e., the ability to decrease tumor cell growth and/or to aid in visualizing tumor cells) in an in vivo model, such as an appropriate tumor cell line, or in a mouse or rat human brain tumor model, as described below. In a preferred embodiment, anti-TM7XN1 protein antibody compounds may be screened using a variety of methods in vitro and in vivo. These methods include, but are not limited to, methods that measure binding affinity to a target, biodistribution of the compound within an animal or cell, or compound mediated cytotoxicity. These and other screening methods known in the art provide information on the ability of a compound to bind to, modulate, or otherwise interact with the specified target and are a measure of the compound's efficacy.

Antibodies that alter the biological activity of TM7XN1 protein may be assayed in functional formats, such as glioblastoma cell culture or mouse/rat CNS tumor model studies. In glioblastoma cell models of activity, expression of the protein is first verified in the particular cell strain to be used. If necessary, the cell line may be stably transfected with a coding sequence of the protein under the control of an appropriate constituent promoter, in order to express the protein at a level comparable to that found in primary tumors. The ability of the glioblastoma cells to survive in the presence of the candidate function-altering anti-protein antibody is then determined. In addition to cell-survival assays, cell migration assays may be utilized to determine the effect of the candidate antibody therapeutic agent on the tumor-like behavior of the cells. Alternatively, if the brain tumor protein target is involved in angiogenesis, assays may be utilized to determine the ability of the candidate antibody therapeutic to inhibit vascular neogenesis, an important function in tumor biology.

The binding affinity of the TM7XN1 antibody may be determined using Biacore SPR technology, as is known in the art. In this method, a first molecule is coupled to a Dextran CM-5 sensor chip (Pharmacia), and the bound molecule is used to capture the antibody being tested. The antigen is then applied at a specific flow rate, and buffer applied at the same flow rate, so that dissociation occurs. The association rate and dissociation rates and corresponding rate constants are determined by using BIA evaluation software. For example, see Malmqvist (1993) Surface plasmon resonance for detection and measurement of antibody-antigen affinity and kinetics. Volume: 5:282-286; and Davies (1994) Nanobiology 3:5-16. Sequential introduction of antibodies permits epitope mapping. Once the antigen has been introduced, the ability of a second antibody to bind to the antigen can be tested. Each reactant can be monitored individually in the consecutive formation of multimolecular complexes, permitting multi-site binding experiments to be performed.

The binding of some ligands to their receptors can result in receptor-mediated internalization. This property may be desirable, e.g. with antibody therapeutics such as immunoliposomes; or undesirable, e.g. with antibody directed enzyme-prodrug therapy (ADEPT), where the enzyme needs to be present at the cell surface to convert non active prodrugs into active cytotoxic molecules.

Similarly, in vivo models for human brain tumors, particularly nude mice/SCID mice model or rat models, have been described, for example see Antunes et al. (2000). *J Histochem Cytochem* 48, 847-58; Price et al. (1999) *Clin Cancer Res* 5, 845-54; and Senner et al. (2000). *Acta Neuropathol (Berl)* 99, 603-8. Once correct expression of the protein in the tumor model is verified, the effect of the candidate anti-protein antibodies on the tumor masses in these models can be evaluated, wherein the ability of the anti-protein antibody candidates to alter protein activity is indicated by a decrease in tumor growth or a reduction in the tumor mass. Thus, antibodies that exhibit the appropriate anti-tumor effect may be selected without direct knowledge of the particular biomolecular role of the protein in oncogenesis.

Arrays

Arrays provide a high throughput technique that can assay a large number of polynucleotides in a sample. In one aspect of the invention, an array is constructed comprising TM7XN1 genetic sequence, proteins or antibodies, and further comprising other sequences of interest, e.g. brain tumor associated sequences, sequences associated with ischemia, with neurological defects, and the like. This technology can be used as a tool to test for differential expression. Arrays can be created by spotting polynucleotide probes onto a substrate (e.g., glass, nitrocellulose, etc.) in a two-dimensional matrix or array having bound probes. The probes can be bound to the substrate by either covalent bonds or by non-specific interactions, such as hydrophobic interactions. Techniques for constructing arrays and methods of using these arrays are described in, for example, Schena et al. (1996) *Proc Natl Acad Sci USA*. 93(20):10614-9; Schena et al. (1995) *Science* 270(5235):467-70; Shalon et al. (1996) *Genome Res.* 6(7):639-45, U.S. Pat. No. 5,807,522, EP 799 897; WO 97/29212; WO 97/27317; EP 785 280; WO 97/02357; U.S. Pat. Nos. 5,593,839; 5,578,832; EP 728 520; U.S. Pat. No. 5,599,695; EP 721 016; U.S. Pat. No. 5,556,752; WO 95/22058; and U.S. Pat. No. 5,631,734.

The probes utilized in the arrays can be of varying types and can include, for example, synthesized probes of relatively short length (e.g., a 20-mer or a 25-mer), cDNA (full length or fragments of gene), amplified DNA, fragments of DNA (generated by restriction enzymes, for example) and reverse transcribed DNA. Both custom and generic arrays can be utilized in detecting differential expression levels. Custom arrays can be prepared using probes that hybridize to particular preselected subsequences of mRNA gene sequences or amplification products prepared from them.

Arrays can be used to, for example, examine differential expression of genes and can be used to determine gene function. For example, arrays can be used to detect differential expression of TM7XN1, where expression is compared between a test cell and control cell. Exemplary uses of arrays are further described in, for example, Pappalarado et al. (1998) *Sem. Radiation Oncol.* 8:217; and Ramsay. (1998) *Nature Biotechnol.* 16:40. Furthermore, many variations on methods of detection using arrays are well within the skill in the art and within the scope of the present invention. For example, rather than immobilizing the probe to a solid support, the test sample can be immobilized on a solid support, which is then contacted with the probe. Additional discussion regarding the use of microarrays in expression analysis can be found, for example, in Duggan, et al., Nature Genetics Supplement 21:10-14 (1999); Bowtell, Nature Genetics Supplement 21:25-32 (1999); Brown and Botstein, Nature Genetics Supplement 21:33-37 (1999); Cole et al., Nature Genetics Supplement 21:38-41 (1999); Debouck and Goodfellow, Nature Genetics Supplement 21:48-50 (1999); Bassett, Jr., et al., Nature Genetics Supplement 21:51-55 (1999); and Chakravarti, Nature Genetics Supplement 21:56-60 (1999).

For detecting expression levels, usually nucleic acids are obtained from a test sample, and either directly labeled, or reversed transcribed into labeled cDNA. The test sample containing the labeled nucleic acids is then contacted with the array. After allowing a period sufficient for any labeled nucleic acid present in the sample to hybridize to the probes, the array is typically subjected to one or more high stringency washes to remove unbound nucleic acids and to minimize nonspecific binding to the nucleic acid probes of the arrays. Binding of labeled sequences is detected using any of a variety of commercially available scanners and accompanying software programs.

For example, if the nucleic acids from the sample are labeled with fluorescent labels, hybridization intensity can be determined by, for example, a scanning confocal microscope in photon counting mode. Appropriate scanning devices are described by e.g., U.S. Pat. No. 5,578,832 to Trulson et al., and U.S. Pat. No. 5,631,734 to Stern et al. and are available from Affymetrix, Inc., under the GeneChip™ label. Some types of label provide a signal that can be amplified by enzymatic methods (see Broude, et al., *Proc. Natl. Acad. Sci. U.S.A.* 91, 3072-3076 (1994)). A variety of other labels are also suitable including, for example, radioisotopes, chromophores, magnetic particles and electron dense particles.

Those locations on the probe array that are hybridized to labeled nucleic acid are detected using a reader, such as described by U.S. Pat. No. 5,143,854, WO 90/15070, and U.S. Pat. No. 5,578,832. For customized arrays, the hybridization pattern can then be analyzed to determine the presence and/or relative amounts or absolute amounts of known mRNA species in samples being analyzed as described in e.g., WO 97/10365.

Diagnostic and Prognostic Methods

The differential expression of TM7XN1 genes and/or gene products in tumors indicates that these can serve as markers for diagnosis, for imaging, as well as for therapeutic applications. In general, such diagnostic methods involve detecting an elevated level of expression of TM7XN1 gene transcripts or gene products in the cells or tissue of an individual or a sample therefrom. A variety of different assays can be utilized to detect an increase in gene expression, including both methods that detect gene transcript and protein levels. More specifically, the diagnostic and prognostic methods disclosed herein involve obtaining a sample from an individual and determining at least qualitatively, and preferably quantitatively, the level of TM7XN1 gene product expression in the sample. Usually this determined value or test value is compared against some type of reference or baseline value.

Nucleic acids or binding members such as antibodies that are specific for polypeptides derived from the sequence of one of the sequences provided in The seqlist are used to screen patient samples for increased expression of the corresponding mRNA or protein, or for the presence of amplified DNA in the cell. Samples can be obtained from a variety of sources. Samples are typically obtained from a human subject. However, the methods can also be utilized with samples obtained from various other mammals, such as primates, e.g. apes and chimpanzees, mice, cats, rats, and other animals. Such samples are referred to as a patient sample.

Samples can be obtained from the tissues or fluids of an individual, as well as from cell cultures or tissue homogenates. For example, samples can be obtained from spinal fluid, or tumor biopsy samples. Also included in the term are derivatives and fractions of such cells and fluids. Samples can also be derived from in vitro cell cultures, including the growth medium, recombinant cells and cell components. Diagnostic samples are collected from an individual that has, or is suspected to have, a brain tumor. The presence of specific markers is useful in identifying and staging the tumor.

Nucleic Acid Screening Methods

Some of the diagnostic and prognostic methods that involve the detection of TM7XN1 transcript begin with the lysis of cells and subsequent purification of nucleic acids from other cellular material, particularly mRNA transcripts. A nucleic acid derived from an mRNA transcript refers to a nucleic acid for whose synthesis the mRNA transcript, or a subsequence thereof, has ultimately served as a template. Thus, a cDNA reverse transcribed from an mRNA, an RNA transcribed from that cDNA, a DNA amplified from the cDNA, an RNA transcribed from the amplified DNA, are all derived from the mRNA transcript and detection of such derived products is indicative of the presence and/or abundance of the original transcript in a sample.

A number of methods are available for analyzing nucleic acids for the presence of a specific sequence, e.g. upregulated or downregulated expression. The nucleic acid may be amplified by conventional techniques, such as the polymerase chain reaction (PCR), to provide sufficient amounts for analysis. The use of the polymerase chain reaction is described in Saiki et al. (1985) *Science* 239:487, and a review of techniques may be found in Sambrook, et al. *Molecular Cloning: A Laboratory Manual*, CSH Press 1989, pp. 14.2-14.33.

A detectable label may be included in an amplification reaction. Suitable labels include fluorochromes, e.g. ALEXA dyes (available from Molecular Probes, Inc.); fluorescein isothiocyanate (FITC), rhodamine, Texas Red, phycoerythrin, allophycocyanin,6-carboxyfluorescein(6-FAM),2,7-dimethoxy-4,5-dichloro-6-carboxyfluorescein (JOE), 6-carboxy-X-rhodamine (ROX), 6-carboxy-2,4,7,4,7-hexachlorofluorescein (HEX), 5-carboxyfluorescein (5-FAM) or N,N,N,N-tetramethyl-6-carboxyrhodamine (TAMRA), radioactive labels, e.g. $^{32}$P, $^{35}$S, $^{3}$H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. amplified, labeled, cloned fragment, etc. is analyzed by one of a number of methods known in the art. Probes may be hybridized to northern or dot blots, or liquid hybridization reactions performed. The nucleic acid may be sequenced by dideoxy or other methods, and the sequence of bases compared to a wild-type sequence. Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility. Fractionation is performed by gel or capillary electrophoresis, particularly acrylamide or agarose gels.

In situ hybridization methods are hybridization methods in which the cells are not lysed prior to hybridization. Because the method is performed in situ, it has the advantage that it is not necessary to prepare RNA from the cells. The method usually involves initially fixing test cells to a support (e.g., the flat surface of a microscope slide or the walls of a microtiter well) and then permeabilizing the cells with an appropriate permeabilizing solution. A solution containing labeled probes is then contacted with the cells and the probes allowed to hybridize. Excess probe is digested, washed away and the amount of hybridized probe measured. This approach is described in greater detail by Nucleic Acid Hybridization: A Practical Approach (Hames, et al., eds., 1987).

A variety of so-called "real time amplification" methods or "real time quantitative PCR" methods can also be utilized to determine the quantity of mRNA present in a sample. Such methods involve measuring the amount of amplification product formed during an amplification process. Fluorogenic nuclease assays are one specific example of a real time quantitation method that can be used to detect and quantitate transcripts. In general such assays continuously measure PCR product accumulation using a dual-labeled fluorogenic oligonucleotide probe—an approach frequently referred to in the literature simply as the "TaqMan" method. Additional details regarding the theory and operation of fluorogenic methods for making real time determinations of the concentration of amplification products are described, for example, in U.S. Pat. No. 5,210,015 to Gelfand, U.S. Pat. No. 5,538,848 to Livak, et al., and U.S. Pat. No. 5,863,736 to Haaland, each of which is incorporated by reference in its entirety.

Polypeptide Screening Methods

Screening for expression of the subject sequences may be based on the functional or antigenic characteristics of the protein. Various immunoassays designed to detect polymorphisms in TM7XN1 protein may be used in screening. Detection may utilize staining of cells or histological sections, performed in accordance with conventional methods, using antibodies or other specific binding members that specifically bind to TM7XN1. The antibodies or other specific binding members of interest are added to a cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Final detection uses a substrate that undergoes a color change in the presence of the peroxidase. The absence or presence of antibody binding may be determined by various methods, including flow cytometry of dissociated cells, microscopy, radiography, scintillation counting, etc.

An alternative method for diagnosis depends on the in vitro detection of binding between antibodies and the polypeptide corresponding to a TM7XN1 sequence in a lysate. Measuring the concentration of the target protein in a sample or fraction thereof may be accomplished by a variety of specific assays. A conventional sandwich type assay may be used, e.g. ELISA. For example, a sandwich assay may first attach specific antibodies to an insoluble surface or support. The particular manner of binding is not crucial so long as it is compatible with the reagents and overall methods of the invention. They may be bound to the plates covalently or non-covalently, preferably non-covalently.

The insoluble supports may be any compositions to which polypeptides can be bound, which is readily separated from soluble material, and which is otherwise compatible with the overall method. The surface of such supports may be solid or porous and of any convenient shape. Examples of suitable insoluble supports to which the receptor is bound include beads, e.g. magnetic beads, membranes and microtiter plates. These are typically made of glass, plastic (e.g. polystyrene), polysaccharides, nylon or nitrocellulose. Microtiter plates are especially convenient because a large number of assays can be carried out simultaneously, using small amounts of reagents and samples.

Patient sample lysates are then added to separately assayable supports (for example, separate wells of a microtiter plate) containing antibodies. Preferably, a series of standards, containing known concentrations of the test protein is assayed in parallel with the samples or aliquots thereof to serve as controls. Preferably, each sample and standard will be added to multiple wells so that mean values can be obtained for each. The incubation time should be sufficient for binding. After incubation, the insoluble support is generally washed of non-bound components. After washing, a solution containing a second antibody is applied. The antibody will bind to one of the proteins of interest with sufficient specificity such that it can be distinguished from other components present. The second antibodies may be labeled to facilitate direct, or indirect quantification of binding. In a preferred embodiment, the antibodies are labeled with a covalently bound enzyme capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art. The incubation time should be sufficient for the labeled ligand to bind available molecules.

After the second binding step, the insoluble support is again washed free of non-specifically bound material, leaving the specific complex formed between the target protein and the specific binding member. The signal produced by the bound conjugate is detected by conventional means. Where an enzyme conjugate is used, an appropriate enzyme substrate is provided so a detectable product is formed.

Other immunoassays are known in the art and may find use as diagnostics. Ouchterlony plates provide a simple determination of antibody binding. Western blots may be performed on protein gels or protein spots on filters, using a detection system specific for the targeted polypeptide, conveniently using a labeling method as described for the sandwich assay.

In some cases, a competitive assay will be used. In addition to the patient sample, a competitor to the targeted protein is added to the reaction mix. The competitor and the target compete for binding to the specific binding partner. Usually, the competitor molecule will be labeled and detected as previously described, where the amount of competitor binding will be proportional to the amount of target protein present. The concentration of competitor molecule will be from about 10 times the maximum anticipated protein concentration to about equal concentration in order to make the most sensitive and linear range of detection.

Imaging In Vivo

In some embodiments, the methods are adapted for imaging use in vivo, e.g., to locate or identify sites where tumor cells are present. In these embodiments, a detectably-labeled moiety, e.g., an antibody, which is specific for TM7XN1 is administered to an individual (e.g., by injection), and labeled cells are located using standard imaging techniques, including, but not limited to, magnetic resonance imaging, computed tomography scanning, and the like.

For diagnostic in vivo imaging, the type of detection instrument available is a major factor in selecting a given radionuclide. The radionuclide chosen must have a type of decay that is detectable by a given type of instrument. In general, any conventional method for visualizing diagnostic imaging can be utilized in accordance with this invention. Another important factor in selecting a radionuclide for in vivo diagnosis is that its half-life be long enough that it is still detectable at the time of maximum uptake by the target tissue, but short enough that deleterious radiation of the host is minimized. A currently used method for labeling with $^{99m}$Tc is the reduction of pertechnetate ion in the presence of a chelating precursor to form the labile $^{99m}$Tc-precursor complex, which, in turn, reacts with the metal binding group of a bifunctionally modified chemotactic peptide to form a $^{99m}$Tc-chemotactic peptide conjugate.

The detectably labeled TM7XN1 specific antibody is used in conjunction with imaging techniques, in order to analyze the expression of the target. In one embodiment, the imaging method is one of PET or SPECT, which are imaging techniques in which a radionuclide is synthetically or locally administered to a patient. The subsequent uptake of the radiotracer is measured over time and used to obtain information about the targeted tissue. Because of the high-energy (γ-ray) emissions of the specific isotopes employed and the sensitivity and sophistication of the instruments used to detect them, the two-dimensional distribution of radioactivity may be inferred from outside of the body.

Among the most commonly used positron-emitting nuclides in PET are included $^{11}$C, $^{13}$N, $^{15}$O, and $^{18}$F. Isotopes that decay by electron capture and/or γ emission are used in SPECT, and include $^{123}$I and $^{99m}$Tc.

Therapeutic/Prophylactic Treatment Methods

Agents that modulate activity of TM7XN1 genes or proteins provide a point of therapeutic or prophylactic intervention, particularly agents that inhibit or upregulate activity of the polypeptide, or expression of the gene. In one embodiment of the invention, an antibody as described above is administered by local administration to brain tissues for treatment of brain tumors, including glioblastoma. This antibody may be a neutralizing antibody, a functional blocker, may bind to and prevent cleavage at the GPS domain, or may pevent multimerization thus affecting signal amplification, or it may preventing ligand binding.

Agents useful in modulating TM7XN1 activity include agents that directly modulate expression, e.g. expression vectors, antisense specific for the targeted polypeptide; and agents that act on the protein, e.g. specific antibodies and analogs thereof, small organic molecules that block catalytic activity, etc.

Methods can be designed to selectively deliver nucleic acids to certain cells. Examples of such cells include, neurons, microglia, astrocytes, endothelial cells, oligodendrocytes, etc. Certain treatment methods are designed to selectively express an expression vector to neuron cells and/or target the nucleic acid for delivery to CNS derived cells (microglia, astrocytes, endothelial cells, oligodendrocytes). One technique for achieving selective expression in CNS derived cells is to operably link the coding sequence to a promoter that is primarily active in CNS derived cells. Examples of such promoters include, but are not limited to, prion protein promoter, calcium-calmodulin dependent protein kinase promoter. Alternatively, or in addition, the nucleic acid can be administered with an agent that targets the nucleic acid to CNS derived cells. For instance, the nucleic acid can be administered with an antibody that specifically binds to a cell-surface antigen on the CNS derived cells or a ligand for a receptor on neuronal cells.

When liposomes are utilized, substrates that bind to a cell-surface membrane protein associated with endocytosis can be attached to the liposome to target the liposome to nerve cells and to facilitate uptake. Examples of proteins that can be attached include capsid proteins or fragments thereof that bind to CNS derived cells, antibodies that specifically bind to cell-surface proteins on CNS derived cells that undergo internalization in cycling and proteins that target intracellular localizations within CNS derived cells (see, e.g., Wu et al. (1987) J. Biol. Chem. 262:4429-4432; and Wagner, et al. (1990) Proc. Natl. Acad. Sci. USA 87:3410-3414). Gene marking and gene therapy protocols are reviewed by Anderson et al. (1992) Science 256:808-813. Various other delivery options can also be utilized. For instance, a nucleic acid containing a sequence of interest can be injected directly into the cerebrospinal fluid. Alternatively, such nucleic acids can be administered by intraventricular injections.

Antisense molecules can be used to down-regulate expression in cells. The antisense reagent may be antisense oligonucleotides (ODN), particularly synthetic ODN having chemical modifications from native nucleic acids, or nucleic acid constructs that express such antisense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996) *Nature Biotechnology* 14:840-844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in vitro or in an animal model. A combination of sequences may also be used, where several regions of the mRNA sequence are selected for antisense complementation.

Antisense oligonucleotides may be chemically synthesized by methods known in the art (see Wagner et al. (1993) supra. and Milligan et al., supra.) Preferred oligonucleotides are chemically modified from the native phosphodiester structure, in order to increase their intracellular stability and binding affinity. A number of such modifications have been described in the literature, which alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The alpha.-anomer of deoxyribose may be used, where the base is inverted with respect to the natural .beta.-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

Compound Screening

Compound screening may be performed using an in vitro model, a genetically altered cell or animal, or purified TM7XN1 protein. One can identify ligands or substrates that bind to, modulate or mimic the action of the encoded polypeptide.

The polypeptides include those encoded by TM7XN1 genes, as well as nucleic acids that, by virtue of the degeneracy of the genetic code, are not identical in sequence to the disclosed nucleic acids, and variants thereof. Variant polypeptides can include amino acid (aa) substitutions, additions or deletions. The amino acid substitutions can be conservative amino acid substitutions or substitutions to eliminate non-essential amino acids, such as to alter a glycosylation site, a phosphorylation site or an acetylation site, or to minimize misfolding by substitution or deletion of one or more cysteine residues that are not necessary for function. Variants can be designed so as to retain or have enhanced biological activity of a particular region of the protein (e.g., a functional domain and/or, where the polypeptide is a member of a protein family, a region associated with a consensus sequence). Variants also include fragments of the polypeptides disclosed herein, particularly biologically active fragments and/or fragments corresponding to functional domains. Fragments of interest will typically be at least about 10 aa to at least about 15 aa in length, usually at least about 50 aa in length, and can be as long as 300 aa in length or longer, but will usually not exceed about 500 aa in length, where the fragment will have a contiguous stretch of amino acids that is identical to a polypeptide encoded by brain tumor associated genes, or a homolog thereof.

Transgenic animals or cells derived therefrom are also used in compound screening. Transgenic animals may be made through homologous recombination, where the normal locus corresponding to TM7XN1 is altered. Alternatively, a nucleic acid construct is randomly integrated into the genome. Vectors for stable integration include plasmids, retroviruses and other animal viruses, YACs, and the like. A series of small deletions and/or substitutions may be made in the coding sequence to determine the role of different exons in enzymatic activity, oncogenesis, signal transduction, etc. Specific constructs of interest include antisense sequences that block expression of the targeted gene and expression of dominant negative mutations. A detectable marker, such as lac Z may be introduced into the locus of interest, where up-regulation of expression will result in an easily detected change in phenotype. One may also provide for expression of the target gene or variants thereof in cells or tissues where it is not normally expressed or at abnormal times of development. By providing expression of the target protein in cells in which it is not normally produced, one can induce changes in cell behavior.

Compound screening identifies agents that modulate function of TM7XN1 polypeptides. Of particular interest are screening assays for agents that have a low toxicity for human cells. A wide variety of assays may be used for this purpose, including labeled in vitro protein-protein binding assays, and the like. Knowledge of the 3-dimensional structure of the encoded protein, derived from crystallization of purified recombinant protein, could lead to the rational design of small drugs that specifically inhibit activity. These drugs may be directed at specific domains.

Two commonly used markers of GPCR activation are intracellular calcium and cAMP. This method can also be used for the identification of functional agonists and antagonists for G-protein coupled receptors (GPCRs). FLIPR (Fluorometric Imaging Plate Reader Molecular Devices Corp) is used to monitor intracellular calcium mobilization. In order to monitor orphan GPCR activity orphan GPCR targets are force coupled to chimeric G-proteins. This enables the measurement of orphan GPCR's that stimulate either the Gq or Gs pathways to be probed in a single well. First, excitation of the Gq-PLC pathway resulting in calcium mobilization is measured in an intact cell utilizing a FLIPR instrument. Subsequently Gs-activation is monitored by lysing the cells and measuring the levels of cAMP using an HTRF method. This type of dual readout reduces reagent costs and compound consumption during ligand fishing screens.

The effect of an agent on an invasion assay may be monitored, for example, to provide a measure of the cells ability to move through a matrix like matrigel in response to a chemoattractant, e.g. 5% fetal bovine serum, etc. Percent Invasion is determined by the number of cells invading through matrigel coated FluoroBlok membrane divided by the number of cells invading through uncoated Fluorblok membrane.

A number of in vitro and in vivo bioassays have been developed to mimic the complex process of angiogenesis. Among these, two assays in particular have been widely used to screen specifically for angiogenic regulatory factors, each mimicking an aspect of angiogenesis; namely, endothelial cell proliferation and migration. The proliferation assay uses cultured capillary endothelial cells and measures either increased cell number or the incorporation of radio-labeled or modified nucleosides to detect cells in S phase. In contrast, the chemotaxis assay separates endothelial cells and a test solution by a porous membrane disc (a Boyden Chamber), such that migration of endothelial cells across the barrier is indicative of a chemoattractant present in the test solution.

Rate of internalization can be measured by coupling a fluorescent tag to the protein for example using the Cellomics Array Scan HCS reader. Rate of association and dissociation can also be measured in a similar fashion. Receptor internalization can be measured by its accumulation in the recycling compartment, and the receptor's decrease in the recycling compartment.

The ability of an agent to affect apoptosis may be determined. Apoptosis can be defined as "gene-directed cellular self-destruction". Cell death can occur by necrosis or apoptosis. There are many ways to measure apoptosis. For example, loss of cell viability, determined by failure to exclude vital dye, or uptake of MTT; DNA fragmentation, in situ tunnel labeling, cell and nuclear morphology, sub G1 peak FACS analysis, cysteine protease activation, inhibition of Bcl2 etc.

Gelatin zymography is a qualitative method to analyze enzymes involved in matrix degradation. It can be combined with fluorogenic substrate assays to demonstrate temporal changes in enzyme concentration and activity. The invasive property of a tumor may be accompanied by the elaboration of proteolytic enzymes, such as collagenases, that degrade matrix material and basement membrane material, to enable the tumor to expand beyond the confines of the particular tissue in which that tumor is located. Elaboration of such enzymes may be by endogenous synthesis within the tumor cells, or may be elicited from adjacent cells or by circulating neutrophils, in which cases the elicitation by the tumor results from chemical messengers elaborated by the tumor and expression of the enzymes occurs at the tumor site or proximal to the tumor.

The effect of an agent on signaling pathways may be determined using reporter assays that well known in the art. Binding by a ligand triggers activation of key cell signaling pathways, such as $p21^{ras}$, MAP kinases, NF-kappaB and cdc42/rac implicated in tumors. The cis reporting system can be used to determine if the gene or protein of interest acts on speciifc enhancer elements while the trans-activator indicates if the gene or protein of interest directly or indirectly may be involved in the phosphorylation and activation of the transcription factor.

The term "agent" as used herein describes any molecule, e.g. protein or pharmaceutical, with the capability of altering or mimicking the physiological function of TM7XN1. Generally a plurality of assay mixtures are run in parallel with different agent concentrations to obtain a differential response to the various concentrations. Typically one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Test agents can be obtained from libraries, such as natural product libraries or combinatorial libraries, for example. A number of different types of combinatorial libraries and methods for preparing such libraries have been described, including for example, PCT publications WO 93/06121, WO 95/12608, WO 95/35503, WO 94/08051 and WO 95/30642, each of which is incorporated herein by reference.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin, etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

Preliminary screens can be conducted by screening for compounds capable of binding to TM7XN1 polypeptide, as at least some of the compounds so identified are likely modulators, e.g. inhibitors or activators. The binding assays usually involve contacting TM7XN1 with one or more test compounds and allowing sufficient time for the protein and test compounds to form a binding complex. Any binding complexes formed can be detected using any of a number of established analytical techniques. Protein binding assays include, but are not limited to, methods that measure co-precipitation, co-migration on non-denaturing SDS-polyacrylamide gels, and co-migration on Western blots (see, e.g., Bennet, J. P. and Yamamura, H. I. (1985) "Neurotransmitter, Hormone or Drug Receptor Binding Methods," in *Neurotransmitter Receptor Binding* (Yamamura, H. I., et al., eds.), pp. 61-89.

The level of expression or activity can be compared to a baseline value. As indicated above, the baseline value can be a value for a control sample or a statistical value that is representative of expression levels for a control population. Expression levels can also be determined for cells that do not express TM7XN1, as a negative control. Such cells generally are otherwise substantially genetically the same as the test cells. Various controls can be conducted to ensure that an observed activity is authentic including running parallel reactions with cells that lack the reporter construct or by not contacting a cell harboring the reporter construct with test compound. Compounds can also be further validated as described below.

Compounds that are initially identified by any of the foregoing screening methods can be further tested to validate the apparent activity. The basic format of such methods involves administering a lead compound identified during an initial screen to an animal that serves as a model for humans and then determining if TM7XN1 is in fact upregulated. The animal models utilized in validation studies generally are mammals. Specific examples of suitable animals include, but are not limited to, primates, mice, and rats.

Active test agents identified by the screening methods described herein that inhibit TM7XN1 activity and/or tumor growth can serve as lead compounds for the synthesis of analog compounds. Typically, the analog compounds are synthesized to have an electronic configuration and a molecular conformation similar to that of the lead compound. Identification of analog compounds can be performed through use of techniques such as self-consistent field (SCF) analysis, configuration interaction (CI) analysis, and normal mode dynamics analysis. Computer programs for implementing these techniques are available. See, e.g., Rein et al., (1989) Computer-Assisted Modeling of Receptor-Ligand Interactions (Alan Liss, New York).

Antibody Conjugates

The anti-TM7XN1 antibodies for use in the present invention may have utility without conjugation when the native activity of the brain tumor protein target is altered in the tumor cell. Such antibodies, which may be selected as described above, may be utilized without conjugation as a therapeutic agent. In another embodiment of the invention, TM7XN1 specific antibodies, which may or may not alter the activity of the target polypeptide, are conjugated to cytotoxic or imaging agents, which add functionality to the antibody.

The anti-TM7XN1 antibodies can be coupled or conjugated to one or more therapeutic cytotoxic or imaging moieties. As used herein, "cytotoxic moiety" is a moiety that inhibits cell growth or promotes cell death when proximate to or absorbed by the cell. Suitable cytotoxic moieties in this regard include radioactive isotopes (radionuclides), chemotoxic agents such as differentiation inducers and small chemotoxic drugs, toxin proteins, and derivatives thereof. "Imaging moiety" (I) is a moiety that can be utilized to increase contrast between a tumor and the surrounding healthy tissue in a visualization technique (e.g., radiography, positron-emission tomography, magnetic resonance imaging, direct or indirect visual inspection). Thus, suitable imaging moieties include radiography moieties (e.g. heavy metals and radiation emitting moieties), positron emitting moieties, magnetic resonance contrast moieties, and optically visible moieties (e.g., fluorescent or visible-spectrum dyes, visible particles, etc.). It will be appreciated by one of ordinary skill that some overlap exists between therapeutic and imaging moieties. For instance $^{212}$Pb and $^{212}$Bi are both useful radioisotopes for therapeutic compositions, but are also electron-dense, and thus provide contrast for X-ray radiographic imaging techniques, and can also be utilized in scintillation imaging techniques.

In general, therapeutic or imaging agents may be conjugated to the anti-TM7XN1 moiety by any suitable technique, with appropriate consideration of the need for pharmokinetic stability and reduced overall toxicity to the patient. A therapeutic agent may be coupled to a suitable antibody moiety either directly or indirectly (e.g. via a linker group). A direct reaction between an agent and an antibody is possible when each possesses a functional group capable of reacting with the other. For example, a nucleophilic group, such as an amino or sulfhydryl group, may be capable of reacting with a carbonyl-containing group, such as an anhydride or an acid halide, or with an alkyl group containing a good leaving group (e.g., a halide). Alternatively, a suitable chemical linker group may be used. A linker group can function as a spacer to distance an antibody from an agent in order to avoid interference with binding capabilities. A linker group can also serve to increase the chemical reactivity of a substituent on a moiety or an antibody, and thus increase the coupling efficiency. An increase in chemical reactivity may also facilitate the use of moieties, or functional groups on moieties, which otherwise would not be possible.

Suitable linkage chemistries include maleimidyl linkers and alkyl halide linkers (which react with a sulfhydryl on the antibody moiety) and succinimidyl linkers (which react with a primary amine on the antibody moiety). Several primary amine and sulfhydryl groups are present on immunoglobulins, and additional groups may be designed into recombinant immunoglobulin molecules. It will be evident to those skilled in the art that a variety of bifunctional or polyfunctional reagents, both homo- and hetero-functional (such as those described in the catalog of the Pierce Chemical Co., Rockford, Ill.), may be employed as a linker group. Coupling may be effected, for example, through amino groups, carboxyl groups, sulfhydryl groups or oxidized carbohydrate residues. There are numerous references describing such methodology, e.g., U.S. Pat. No. 4,671,958. As an alternative coupling method, cytotoxic or imaging moieties may be coupled to the anti-$T_{BT}$ antibody moiety through a an oxidized carbohydrate group at a glycosylation site, as described in U.S. Pat. Nos. 5,057,313 and 5,156,840. Yet another alternative method of coupling the antibody moiety to the cytotoxic or imaging moiety is by the use of a non-covalent binding pair, such as streptavidin/biotin, or avidin/biotin. In these embodiments, one member of the pair is covalently coupled to the antibody moiety and the other member of the binding pair is covalently coupled to the cytotoxic or imaging moiety.

Where a cytotoxic moiety is more potent when free from the antibody portion of the immunoconjugates of the present invention, it may be desirable to use a linker group that is cleavable during or upon internalization into a cell, or which is gradually cleavable over time in the extracellular environment. A number of different cleavable linker groups have been described. The mechanisms for the intracellular release of a cytotoxic moiety agent from these linker groups include cleavage by reduction of a disulfide bond (e.g., U.S. Pat. No. 4,489,710), by irradiation of a photolabile bond (e.g., U.S.

Pat. No. 4,625,014), by hydrolysis of derivatized amino acid side chains (e.g., U.S. Pat. No. 4,638,045), by serum complement-mediated hydrolysis (e.g., U.S. Pat. No. 4,671,958), and acid-catalyzed hydrolysis (e.g., U.S. Pat. No. 4,569,789).

Two or more cytotoxic and/or imaging moieties may be conjugated to an antibody, where the conjugated moieties are the same or different. By poly-derivatizing the anti-TM7XN1 antibody, several cytotoxic strategies can be simultaneously implemented; an antibody may be made useful as a contrasting agent for several visualization techniques; or a therapeutic antibody may be labeled for tracking by a visualization technique. Immunoconjugates with more than one moiety may be prepared in a variety of ways. For example, more than one moiety may be coupled directly to an antibody molecule, or linkers which provide multiple sites for attachment (e.g., dendrimers) can be used. Alternatively, a carrier with the capacity to hold more than one cytotoxic or imaging moiety can be used.

A carrier may bear the cytotoxic or imaging moiety in a variety of ways, including covalent bonding either directly or via a linker group, and non-covalent associations. Suitable covalent-bond carriers include proteins such as albumins (e.g., U.S. Pat. No. 4,507,234), peptides, and polysaccharides such as aminodextran (e.g., U.S. Pat. No. 4,699,784), each of which have multiple sites for the attachment of moieties. A carrier may also bear an agent by non-covalent associations, such as non-covalent bonding or by encapsulation, such as within a liposome vesicle (e.g., U.S. Pat. Nos. 4,429,008 and 4,873,088). Encapsulation carriers are especially useful for imaging moiety conjugation to anti-TM7XN1 antibody moieties for use in the invention, as a sufficient amount of the imaging moiety (dye, magnetic resonance contrast reagent, etc.) for detection may be more easily associated with the antibody moiety. In addition, encapsulation carriers are also useful in chemotoxic therapeutic embodiments, as they can allow the therapeutic compositions to gradually release a chemotoxic moiety over time while concentrating it in the vicinity of the tumor cells.

Carriers and linkers specific for radionuclide agents (both for use as cytotoxic moieties or positron-emission imaging moieties) include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis. Such chelation carriers are also useful for magnetic spin contrast ions for use in magnetic resonance imaging tumor visualization methods, and for the chelation of heavy metal ions for use in radiographic visualization methods.

Preferred radionuclides for use as cytotoxic moieties are radionuclides that are suitable for pharmacological administration. Such radionuclides include $^{123}$I, $^{125}$I, $^{131}$I, $^{90}$Y, $^{211}$At, $^{67}$Cu, $^{186}$Re, $^{188}$Re, $^{212}$Pb, and $^{212}$Bi. Iodine and astatine isotopes are more preferred radionuclides for use in the therapeutic compositions of the present invention, as a large body of literature has been accumulated regarding their use. $^{131}$I is particularly preferred, as are other β-radiation emitting nuclides, which have an effective range of several millimeters. $^{123}$I, $^{125}$I, or $^{211}$At may be conjugated to antibody moieties for use in the compositions and methods utilizing any of several known conjugation reagents, including Iodogen, N-succinimidyl 3-[$^{211}$At]astatobenzoate, N-succinimidyl 3-[$^{131}$I]iodobenzoate (SIB), and, N-succinimidyl 5-[$^{131}$I]iodob-3-pyridinecarboxylate (SIPC). Any iodine isotope may be utilized in the recited iodo-reagents. Radionuclides can be conjugated to anti-TM7XN1 antibody moieties by suitable chelation agents known to those of skill in the nuclear medicine arts.

Preferred chemotoxic agents include small-molecule drugs such as carboplatin, cisplatin, vincristine, taxanes such as paclitaxel and doceltaxel, hydroxyurea, gemcitabine, vinorelbine, irinotecan, tirapazamine, matrilysin, methotrexate, pyrimidine and purine analogs, and other suitable small toxins known in the art. Preferred chemotoxin differentiation inducers include phorbol esters and butyric acid. Chemotoxic moieties may be directly conjugated to the anti-TM7XN1 antibody moiety via a chemical linker, or may encapsulated in a carrier, which is in turn coupled to the anti-TM7XN1 antibody moiety.

Chemotherapy is helpful in controlling high-grade gliomas. A common combination of chemotherapeutics is "PCV", which refers to the three drugs: Procarbazine, CCNU, and Vincristine. Temozolomide (Temodar) is approved by the FDA for treatment of anaplastic astrocytoma, and this drug is now widely used for high-grade gliomas. Neupogen may be administered to patients whose white blood counts fall to very low levels after chemotherapy.

Preferred toxin proteins for use as cytotoxic moieties include ricins A and B, abrin, diphtheria toxin, bryodin 1 and 2, momordin, trichokirin, cholera toxin, gelonin, Pseudomonas exotoxin, Shigella toxin, pokeweed antiviral protein, and other toxin proteins known in the medicinal biochemistry arts. The nontoxic ricin B chain is the moiety that binds to cells while the A chain is the toxic portion that inactivates protein synthesis—but only after delivery to the cytoplasm by the disulfide-linked B chain which binds to galactose-terminal membrane proteins. Abrin, diphtheria toxin, and Pseudomonas exotoxins all have similar 2-chain components; with one chain mediating cell membrane binding and entry and the toxic enzymatic A chain. Cholera has a pentameric binding subunit coupled to the toxic A chain. As these toxin agents may elicit undesirable immune responses in the patient, especially if injected intravascularly, it is preferred that they be encapsulated in a carrier for coupling to the anti-TM7XN1 antibody moiety.

Preferred radiographic moieties for use as imaging moieties in the present invention include compounds and chelates with relatively large atoms, such as gold, iridium, technetium, barium, thallium, iodine, and their isotopes. It is preferred that less toxic radiographic imaging moieties, such as iodine or iodine isotopes, be utilized in the compositions and methods of the invention. Examples of compositions that may be utilized for x-ray radiography are described in U.S. Pat. No. 5,709,846, incorporated fully herein by reference. Such moieties may be conjugated to the anti-TM7XN1 antibody moiety through an acceptable chemical linker or chelation carrier. In addition, radionuclides that emit radiation capable of penetrating the skull may be useful for scintillation imaging techniques. Suitable radionuclides for conjugation include $^{99}$Tc, $^{111}$In, and $^{67}$Ga. Positron emitting moieties for use in the present invention include $^{18}$F, which can be easily conjugated by a fluorination reaction with the anti-TM7XN1 antibody moiety according to the method described in U.S. Pat. No. 6,187,284.

Preferred magnetic resonance contrast moieties include chelates of chromium(III), manganese(II), iron(II), nickel (II), copper(II), praseodymium(III), neodymium(III), samarium(III) and ytterbium(III) ion. Because of their very strong magnetic moment, the gadolinium(III), terbium(III), dysprosium(III), holmium(III), erbium(III), and iron(III) ions are especially preferred. Examples of such chelates, suitable for magnetic resonance spin imaging, are described in U.S. Pat. No. 5,733,522, incorporated fully herein by reference. Nuclear spin contrast chelates may be conjugated to the anti-TM7XN1 antibody moieties through a suitable chemical linker.

Optically visible moieties for use as imaging moieties include fluorescent dyes, or visible-spectrum dyes, visible particles, and other visible labeling moieties. Fluorescent dyes such as ALEXA dyes, fluorescein, coumarin, rhodamine, bodipy Texas red, and cyanine dyes, are useful when sufficient excitation energy can be provided to the site to be inspected visually. Endoscopic visualization procedures may be more compatible with the use of such labels. For many procedures where imaging agents are useful, such as during an operation to resect a brain tumor, visible spectrum dyes are preferred. Acceptable dyes include FDA-approved food dyes and colors, which are non-toxic, although pharmaceutically acceptable dyes which have been approved for internal administration are preferred. In preferred embodiments, such dyes are encapsulated in carrier moieties, which are in turn conjugated to the anti-TM7XN1 antibody. Alternatively, visible particles, such as colloidal gold particles or latex particles, may be coupled to the anti-TM7XN1 antibody moiety via a suitable chemical linker.

Pharmaceutical Formulations

One strategy for drug delivery through the blood brain barrier (BBB) entails disruption of the BBB, either by osmotic means such as mannitol or leukotrienes, or biochemically by the use of vasoactive substances such as bradykinin. The potential for using BBB opening to target specific agents to brain tumors is also an option. A BBB disrupting agent can be co-administered with the therapeutic or imaging compositions of the invention when the compositions are administered by intravascular injection. Other strategies to go through the BBB may entail the use of endogenous transport systems, including carrier-mediated transporters such as glucose and amino acid carriers, receptor-mediated transcytosis for insulin or transferrin, and active efflux transporters such as p-glycoprotein. Active transport moieties may also be conjugated to the therapeutic or imaging compounds for use in the invention to facilitate transport across the epithelial wall of the blood vessel. Alternatively, drug delivery behind the BBB is by intrathecal delivery of therapeutics or imaging agents directly to the cranium, as through an Ommaya reservoir.

Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990).

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from cell culture and/or animal studies can be used in formulating a range of dosages for humans. The dosage of the active ingredient typically lines within a range of circulating concentrations that include the $ED_{50}$ with low toxicity. The dosage can vary within this range depending upon the dosage form employed and the route of administration utilized.

The pharmaceutical compositions described herein can be administered in a variety of different ways. Examples include administering a composition containing a pharmaceutically acceptable carrier via oral, intranasal, rectal, topical, intraperitoneal, intravenous, intramuscular, subcutaneous, subdermal, transdermal, intrathecal, and intracranial methods.

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

The active ingredient, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

The compositions of the invention may be administered using any medically appropriate procedure, e.g., intravascular (intravenous, intraarterial, intracapillary) administration, injection into the cerebrospinal fluid, intracavity or direct injection in the tumor. Intrathecal administration maybe carried out through the use of an Ommaya reservoir, in accordance with known techniques. (F. Balis et al., Am J. Pediatr. Hematol. Oncol. 11, 74, 76 (1989). For the imaging compositions of the invention, administration via intravascular injection is preferred for pre-operative visualization of the tumor. Post-operative visualization or visualization concurrent with an operation may be through intrathecal or intracavity administration, as through an Ommaya reservoir, or also by intravascular administration.

One method for administration of the therapeutic compositions of the invention is by deposition into the inner cavity of a cystic tumor by any suitable technique, such as by direct injection (aided by stereotaxic positioning of an injection syringe, if necessary) or by placing the tip of an Ommaya reservoir into a cavity, or cyst, for administration. Where the tumor is a solid tumor, the antibody may be administered by first creating a resection cavity in the location of the tumor. This procedure differs from an ordinary craniotomy and tumor resection only in a few minor respects. As tumor resection is a common treatment procedure, and is often indicated to relieve pressure, administration of the therapeutic compositions of the invention can be performed following tumor resection. Following gross total resection in a standard neurosurgical fashion, the cavity is preferable rinsed with saline until all bleeding is stopped by cauterization. Next the pia-arachnoid membrane, surrounding the tumor cavity at the surface, is cauterized to enhance the formation of fibroblastic reaction and scarring in the pia-arachnoid area. The result is the formation of an enclosed, fluid-filled cavity within the brain tissue at the location from where the tumor was removed. After the cyst has been formed, either the tip of an Ommaya reservoir or a micro catheter, which is connected to a pump device and allows the continuos infusion of an antibody solution into the cavity, can be placed into the cavity. See, e.g., U.S. Pat. No. 5,558,852, incorporated fully herein by reference.

Alternatively, a convection-enhanced delivery catheter may be implanted directly into the tumor mass, into a natural or surgically created cyst, or into the normal brain mass. Such convection-enhanced pharmaceutical composition delivery devices greatly improve the diffusion of the composition throughout the brain mass. The implanted catheters of these delivery devices utilize high-flow microinfusion (with flow rates in the range of about 0.5 to 15.0 µl/minute), rather than diffusive flow, to deliver the therapeutic or imaging composition to the brain and/or tumor mass. Such devices are described in U.S. Pat. No. 5,720,720, incorporated fully herein by reference.

The effective amount of a therapeutic composition to be given to a particular patient will depend on a variety of factors, several of which will be different from patient to patient. A competent clinician will be able to determine an effective amount of a therapeutic agent to administer to a patient to retard the growth and promote the death of tumor cells, or an effective amount of an imaging composition to administer to a patient to facilitate the visualization of a tumor. Dosage of the antibody-conjugate will depend on the treatment of the tumor, route of administration, the nature of the therapeutics, sensitivity of the tumor to the therapeutics, etc. Utilizing $LD_{50}$ animal data, and other information available for the conjugated cytotoxic or imaging moiety, a clinician can determine the maximum safe dose for an individual, depending on the route of administration. For instance, an intravenously administered dose may be more than an intrathecally administered dose, given the greater body of fluid into which the therapeutic composition is being administered. Similarly, compositions which are rapidly cleared from the body may be administered at higher doses, or in repeated doses, in order to maintain a therapeutic concentration. Imaging moieties are typically less toxic than cytotoxic moieties and may be administered in higher doses in some embodiments. Utilizing ordinary skill, the competent clinician will be able to optimize the dosage of a particular therapeutic or imaging composition in the course of routine clinical trials.

Typically the dosage will be 0.001 to 100 milligrams of conjugate per kilogram subject body weight. Doses in the range of 0.01 to 1 mg per kilogram of patient body weight may be utilized for a radionuclide therapeutic composition which is administered intrathecally. Relatively large doses, in the range of 0.1 to 10 mg per kilogram of patient body weight, may used for imaging conjugates with a relatively non-toxic imaging moiety. The amount utilized will depend on the sensitivity of the imaging method, and the relative toxicity of the imaging moiety. In a therapeutic example, for example where the therapeutic composition comprises a $^{131}$I cytotoxic moiety, the dosage to the patient will typically start at a lower range of 10 mCi, and go up to 100, 300 or even 500 mCi. Stated otherwise, where the therapeutic agent is $^{131}$I, the dosage to the patient will typically be from 5,000 Rads to 100,000 Rads (preferably at least 13,000 Rads, or even at least 50,000 Rads). Doses for other radionuclides are typically selected so that the tumoricidal dose will be equivalent to the foregoing range for $^{131}$I. Similarly, chemotoxic or toxin protein doses may be scaled accordingly.

The compositions can be administered to the subject in a series of more than one administration. For therapeutic compositions, regular periodic administration (e.g., every 2-3 days) will sometimes be required, or may be desirable to reduce toxicity. For therapeutic compositions which will be utilized in repeated-dose regimens, antibody moieties which do not provoke immune responses are preferred. The imaging antibody conjugate compositions may be administered at an appropriate time before the visualization technique. For example, administration within an hour before direct visual inspection may be appropriate, or administration within twelve hours before an MRI scan may be appropriate. Care should be taken, however, to not allow too much time to pass between administration and visualization, as the imaging compound may eventually be cleared from the patient's system.

In addition to the use of imaging antibody conjugates for simple visualization, these compositions may be utilized as a "dry run" for more toxic cytotoxic antibody conjugates. If the same antibody moiety is utilized for the imaging conjugate as for the therapeutic conjugate, the physician may first use a visualization technique to determine precisely where in the brain the cytotoxic conjugate will concentrate. If a sufficient degree of tissue selectivity is not achieved (e.g., if the tumor cells are too disperse in the normal tissue, or if the particular brain tumor protein target chosen is not sufficiently overexpressed in the particular patient's tumor cells), then the physician may choose another brain tumor protein target. The provision of numerous brain tumor protein targets by the present invention, along with both imaging and therapeutic agents, allows a high degree of flexibility in designing an effective treatment regimen for the individual patient.

Combination Therapies

Brain tumors tend to be heterogeneous in character, and pervasive throughout the brain tissue. This combination often makes them difficult to treat. In some cases, it may be preferred to use various combinations of therapeutic or imaging agents, in order to more fully target all of the cells exhibiting tumorigenic characteristics. Such combination treatments may be by administering blended antibody therapeutic or imaging compositions, individually prepared as described above, and administering the blended therapeutic to the patient as described. The skilled administering physician will be able to take such factors as combined toxicity, and individual agent efficacy, into account when administering such combined agents. Additionally, those of skill in the art will be able to screen for potential cross-reaction with each other, in order to assure full efficacy of each agent.

Alternatively, several individual brain tumor protein target compositions may be administered simultaneously or in succession for a combined therapy. This may be desirable to avoid accumulated toxicity from several antibody conjugate reagents, or to more closely monitor potential adverse reactions to the individual antibody reagents. Thus, cycles such as where a first antibody therapeutic agent is administered on day one, followed by a second on day two, then a period with out administration, followed by re-administration of the antibody therapeutics on different successive days, is comprehended within the present invention.

The diagnostic imaging of TM7XN1 can provide for "molecular endpoints" to determine the efficacy of therapy, where the therapy can be specifically directed against TM7XN1, or may be a general chemotherapy.

Cancer Vaccines

TM7XN1 protein finds use in eliciting a immune response in an autologous, allogeneic or xenogeneic host. For example where a tumor cell specifically expresses the protein, or over-expresses the protein relative to normal cells, a cytolytic immune response may be induced, where the tumor cell is preferentially killed. The antigen for such purposes may be from the same or a different species. As used herein, the term antigen is intended to refer to a molecule capable of eliciting an immune response in a mammalian host, which may be a humoral immune response, i.e. characterized by the production of antigen-specific antibodies, or a cytotoxic immune response, i.e. characterized by the production of antigen specific cytotoxic T lymphocytes.

The portion of the antigen bound by the antibody or T cell receptor is referred to as an epitope. Antigens, particular complex antigens such as polypeptides, usually comprise multiple epitopes. Where the antigen is a protein, linear epitopes range from about 5 to 20 amino acids in length. Antibodies and T cell receptor may also recognize conformational determinants formed by non-contiguous residues on an antigen, and an epitope can therefore require a larger fragment of the antigen to be present for binding, e.g. a protein domain, or substantially all of a protein sequence. It will therefore be appreciated that a therapeutic protein, which may be several hundred amino acids in length, can comprise a number of distinct epitopes.

Several methods exist which can be used to induce an immune response against weakly antigenic protein, i.e. autologous proteins, etc. The immunogen is usually delivered in vivo to elicit a response, but in some cases it is advantageous to prime antigen presenting cells, e.g. dendritic cells, ex vivo prior to introducing them into the host animal.

In the preparation of the antigen, a TM7XN1 protein or fragments thereof is expressed and purified as is known in the art. Alternatively, fragments of TM7XN1 may be chemically synthesized. In order to produce an immune response, the protein may be made as a fusion protein or otherwise conjugated to another polypeptide, and may be chemically modified or mixed with an adjuvant.

Examples of conjugates, which may utilize peptide linkage or other linkage to joint the molecules, include, for example KLH, pre-S HbsAg or cytokines or chemokines such as, for example interferon inducible protein 10 (IP-10), monocyte chemotactic protein 3 (MCP-3), interleukin-1, -2 and -8, granulocyte macrophage-colony stimulating factor (GM-CSF), etc, or may be chemically modified. Examples of suitable fusion chemokines and methods for antigen preparation and immunization are provided in Biragyn et al (Immunol Rev (1990) 170:115-126); Biragyn et al (Nature Biotechnology (1999) 17:253-258 and Tao et al (1993) Nature 362:755-695).

The polypeptide antigens may be mixed with an adjuvant that will augment specific immune reponses to the antigen. Many different types of adjuvants are known in the art and may include e.g. alum, stearyl tyrosine, saponin, monophosphoryl lipid A (MPL-A), muramyl tripeptide phosphatidylethanolamine (MTP-PE) etc. Adjuvants may also contain cytokines, such as interleukin 1 (IL1), interleukin 2 (IL2) other interleukins, TNFα, and γ-interferon, granulocyte macrophage-colony stimulating factor, tumor necrosis factor etc. Adjuvants may also contain other moieties such as cholera toxin B subunit, whole cell killed mycobacteria, *Bordetella pertussis* components, diptheria toxins and the like. Vaccine antigens may be presented using microspheres, liposomes, may be produced using an immunostimulating complex (ISCOM), as is known in the art.

Where an ex vivo antigen loading step is included, dendritic cells are isolated from an individual, using known methods, and incubated with the peptide antigen, preferably fused to a cytokine such as GM-CSF. The dendritic cell preparation may then be fractionated and administered to the host by intravenous or central injection according to established procedures (e.g., infusion over 30 to 60 minutes). The responsiveness of the subject to this treatment may measured by monitoring the induction of a cytolytic T-cell response, a helper T-cell response and antibody response towards the antigen in peripheral blood mononuclear cells by methods well known in the art. The disclosures of U.S. Pat. Nos. 5,851,756, 6,080,409, 5,994,126 and 5,972,334 are herein incorporated by reference in their entirety.

Experimental

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

EXAMPLE 1

Identification of Differentially Expressed Sequences

Brain Tumors: Tumor tissue, confirmed as glioblastoma grade IV by neuropathology, from an unknown patient was snap frozen in the operation hall and served as experimental sample. Human whole brain tissue (Clontech Laboratories, Palo Alto, USA) served as control sample. Poly-A$^+$ RNA prepared from the cells was converted into double-stranded cDNA (dscDNA) and normalized as described in co-pending U.S. patent application Ser. No. 09/627,362, filed on Jul. 7, 2000. Subtractive hybridization was carried out using the dscDNA from tumors with an excess of dscDNA prepared from the same region of a non-cancerous brain. Differentially expressed gene fragments were cloned into a plasmid vector, and the resulting library was transformed into E. coli cells. Inserts of recombinant clones were amplified by the polymerase chain reaction (PCR). The PCR products (fragments of 200-2000 bp in size) were sequenced using an oligonucleotide complementary to common vector sequences. The resulting sequence information was compared to public databases using the BLAST (blastn) and Smith Waterman algorithm. The differentially expressed sequences thus identified is provided as SEQ ID NO:1, TM7XN1.

TM7XN1 expression profile. The gene encoding TM7XN1 was determined to be upregulated by a factor of 1.905 in a panel of 14 GBM tumor samples, using the AGY imAGYne discovery platform. The p-score for the annotation was 1.6E-83. The increase in mRNA expression level was confirmed using quantitative PCR and in situ hybridization on a panel of normal brain and brain tumor samples. Because mRNA measurements and cDNA arrays do not necessarily accurately reflect the magnitude of protein expression, this target was studied by additional means.

Rabbit polyclonal antibodies were generated against a peptide sequence mapping to the extracellular N-terminus of TM7XN1. These antibodies were proven useful for the analysis of TM7XN1 protein. TM7XN1 protein expression was examined by Western blot of a collection of human glioblastoma derived cell lines, lung, liver, brain and GBM tissue (shown in FIG. 1). This analysis demonstrates that TM7XN1 is upregulated in GBM tumor tissue and is differentially expressed in glioma cell lines.

Figure 2A:
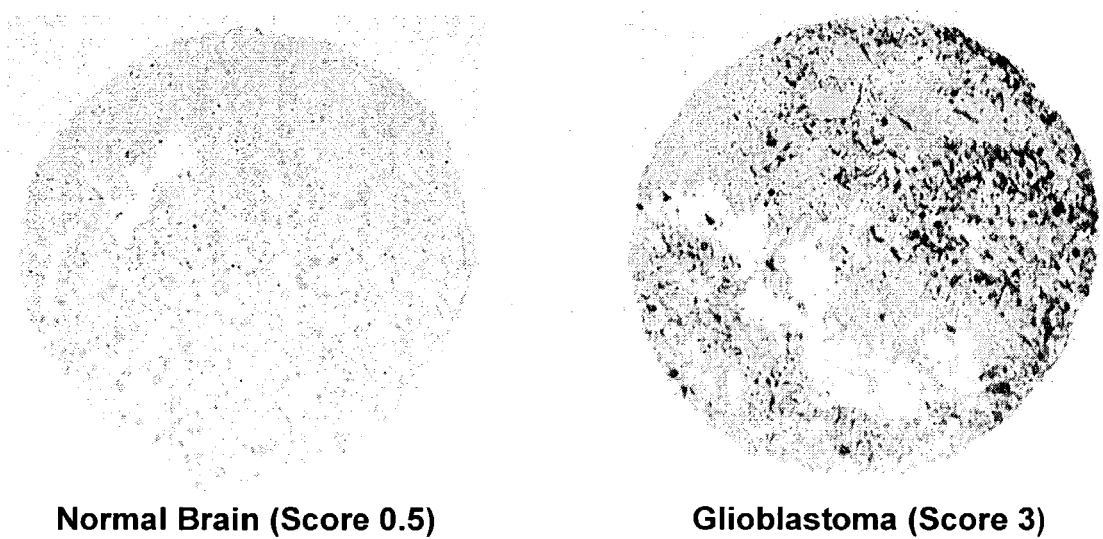
Figure 2A:
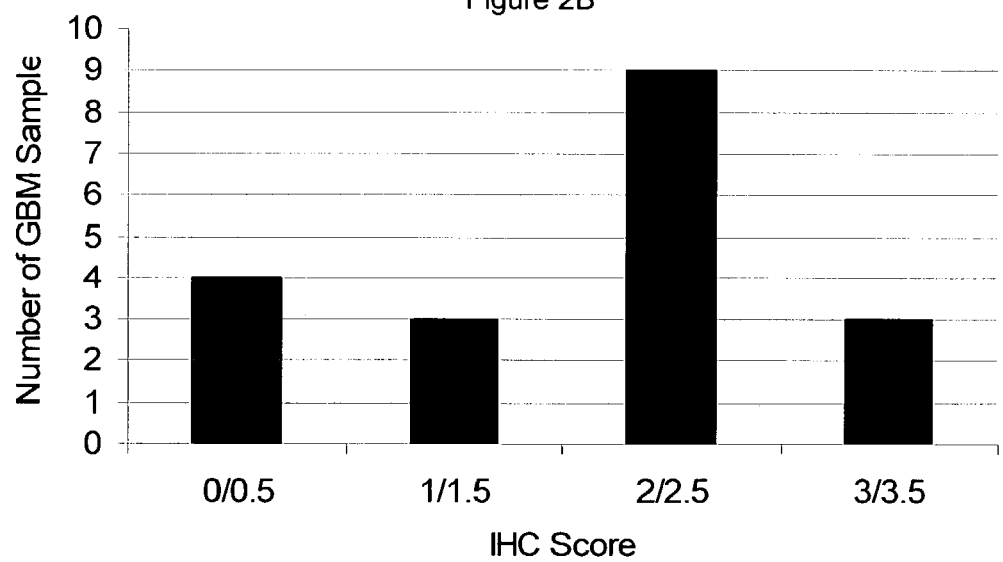

The localization of TM7XN1 protein was analyzed by immunohistochemistry on paraffin sections of primary tumors (shown in FIGS. 2a and 2b). In this study 15 out of 19 GBM tumors (79%) stained positive for TM7XN1. Very low levels of expression were identified in normal brain sections. In addition IHC analysis of a panel of normal human tissue indicated that samples from heart, adrenal gland, and kidney had low to moderate levels of expression. Other tissues (lymph node, colon, liver, testicle, spleen and thyroid) did not have detectable levels of TM7XN1 positive staining. Consistent with our Western blot analysis, these results clearly demonstrate the upregulation of TM7XN1 protein in GBM. Therefore TM7XN1 is an excellent marker for GBM.

Data demonstrates that TM7XN1 is also expressed in other tissues, albeit at lower levels, and may play a role similar to that in the brain. As shown in Table 1, the sequence is also expressed in adenocarcinoma, renal cell carcinomas and non-melanoma cancers).

TABLE 1

Expression of TM7XN1 in human cancers

| Cancer Type | Example of Tumor Tissue | % TM7XN1 positive tumors |
| --- | --- | --- |
| Adenocarcinoma | Colon | 50% |
| Renal Cell Carcinoma | Kidney | 37% |
| Non melanoma Carcinoma | Mouth/Palate/lips/mucous membranes | 43% |

In a survey of human cancer tissues, on Landmark™ High Density cancer survey Tissue Microarray (Ambion) using immunohistochemistry with antibodies directed to TM7XN1 protein, several tumors demonstrated positive staining/expression. The type of cancers most often associated with TM7XN1 expression are listed in the table (adenocarcinoma, renal cell carcinoma, and non melanoma carcinoma which includes basal and squamous cell carcinoma). An example of the tumor tissue type (colon, kidney and mouth/palate) and the percentage of TM7XN1 positive tumors within the group are given. TM7XN1 protein expression is found in a number of human cancers and may be associated with tumor biology.

Figure 3:
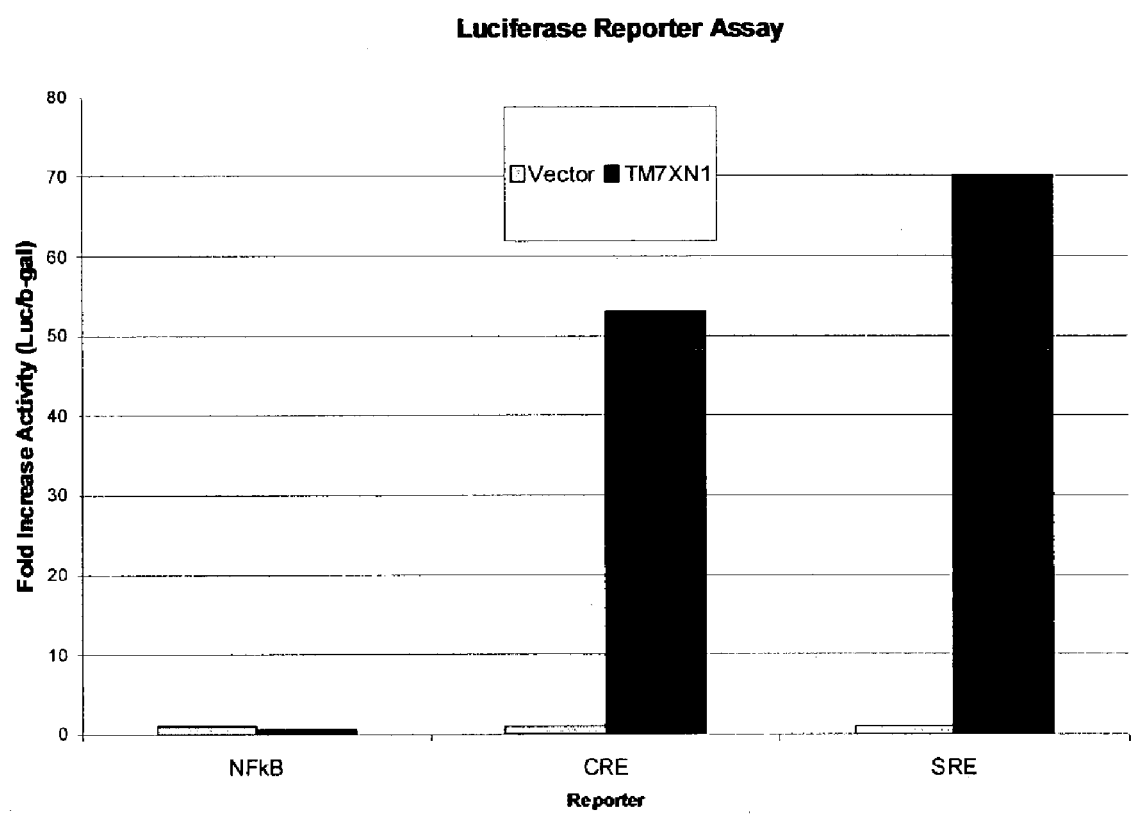
FIG. 3. Activation of downstream transcription factors by transient overexpression of TM7XN1. HEK-293 were transiently transfected with vector control or TM7XN1 along with the reporter construct. The fold increase in luciferase activity was normalized to β-galactosidase activity.

TM7XN1 Functional Validation. The full length TM7XN1 was cloned using RT-PCR from a human adult brain cDNA library. The constructs derived from this cDNA are expressed as either a FLAG epitope tagged or untagged protein. In order to determine the function of TM7XN1, it was transiently co-transfected human HEK-293 cells with TM7XN1 and a panel of luciferase reporter constructs along with a β-galactosidase transfection control. These experiments allow determination of whether TM7XN1 is functional and if it is able to activate known signaling pathways. These measurements allow the indirect study of TM7XN1, function despite the absence of a known ligand. The data indicate that TM7XN1 activates the CREB Response Element (CRE-luciferase) as well as the Serum Response Element (SRE-luciferase) (shown in FIG. 3). NF-κB reporter was not activated by TM7XN1. Therefore TM7XN1 transient overexpression leads to the activation of signaling cascades culminating in the translocation of CREB and SRE into the nucleus where they can modulate gene transcription. These pathways have been implicated in a number of cell functions, including the growth of tumors.

Human glioblastoma derived cells were transfected with control siRNA. Cell proliferation was measured three days later. TM7XN1 siRNA transfected cells proliferated approximately 26% more slowly than control cells, indicating the role of TM7XN1 in tumor cell growth.

The foregoing is intended to be illustrative of the embodiments of the present invention, and are not intended to limit the invention in any way. Although the invention has been described with respect to specific modifications, the details thereof are not to be construed as limitations, for it will be apparent that various equivalents, changes and modifications may be resorted to without departing from the spirit and scope thereof and it is understood that such equivalent embodiments are to be included herein. All publications and patent applications are herein incorporated by reference to the same extent as if each individual publication or patent application was specifically and individually indicated to be incorporated by reference.

What is claimed is:

1. A method for identifying an agent that modulates an activity of TM7XN1 in an adenocarcinoma cell expressing TM7XN1, the method comprising:
   contacting a candidate agent with an adenocarcinoma cell expressing a TM7XN1 polypeptide comprising the amino acid sequence set forth in SEQ ID No:2; and
   determining whether there is an effect on the cell, indicating that the agent modulates an activity of TM7XN1.

2. The method of claim 1, wherein the agent downregulates or upregulates expression of TM7XN1.

3. The method of claim 1, wherein the agent inhibits or increases an activity of TM7XN1.

4. A method for identifying an agent that modulates an activity of TM7XN1 in a non-melanoma skin cancer cell expressing TM7XN1, the method comprising:
   contacting a candidate agent with a non-melanoma skin cancer cell expressing a TM7XN1 polypeptide comprising the amino acid sequence set forth in SEQ ID No:2; and
   determining whether there is an effect on the cell, indicating that the agent modulates an activity of TM7XN.

5. The method of claim 4, wherein the agent downregulates or upregulates expression of TM7XN1.

6. The method of claim 4, wherein the agent inhibits or increases activity of TM7XN1.

7. A method for identifying an agent that modulates activity of TM7XN1 in a renal carcinoma cell expressing TM7XN1, the method comprising:
   contacting a candidate agent with a renal carcinoma cell expressing a TM7XN1 polypeptide comprising the amino acid sequence set forth in SEQ ID No:2; and
   determining whether there is an effect on the cell, indicating that the agent modulates an activity of TM7XN.

8. The method of claim 7, wherein the agent downregulates or upregulates expression of TM7XN1.

9. The method according to claim 7, wherein the agent inhibits or increases an activity of TM7XN1.

10. The method of claim 1, wherein modulation of TM7XN1 is measured by a change in intracellular calcium mobilization in said cell in an in vitro assay.

11. The method of claim 1, wherein modulation of TM7XN1 is measured by a said change in concentration of cAMP.

12. The method of claim 1, wherein modulation of TM7XN1 is measured by the ability of the cell to move through a matrix in an in vitro assay.

13. The method according to claim 1, wherein modulation of TM7XN1 is measured by inhibition of apoptosis of said cells.

14. The method according to claim 1, wherein modulation of TM7XN1 is measured by the expression of enzymes involved in matrix degradation in an in vitro assay.

15. The method of claim 4, wherein modulation of TM7XN1 is measured by a change in intracellular calcium mobilization in said cell in an in vitro assay.

16. The method of claim 4, wherein modulation of TM7XN1 is measured by a change in concentration of cAMP.

17. The method of claim 4, wherein modulation of TM7XN1 is measured by the ability of the cell to move through a matrix in an in vitro invasion assay.

18. The method according to claim 4, wherein modulation of TM7XN1 is measured by inhibition of apoptosis of the cell.

19. The method according to claim 4, wherein modulation of TM7XN1 is measured by the expression of enzymes involved in matrix degradation in an in vitro assay.

20. The method of claim 7, wherein modulation of TM7XN1 is measured by a change in intracellular calcium mobilization in said cell in an in vitro assay.

21. The method of claim 7, wherein modulation of TM7XN1 is measured by a change in concentration of cAMP.

22. The method according to claim 7, wherein modulation of TM7XN1 is measured by a change in the ability of the cell to move through a matrix in an in vitro invasion assay.

23. The method according to claim 7, wherein modulation of TM7XN1 is measured by inhibition of apoptosis of said cells.

24. The method according to claim 7, wherein modulation of TM7XN1 is measured by the expression of enzymes involved in matrix degradation in an in vitro assay.

* * * * *